(12) United States Patent
Gopman

(10) Patent No.: US 9,714,991 B2
(45) Date of Patent: Jul. 25, 2017

(54) SUSCEPTOMETER AND PROCESS FOR DETERMINING MAGNETIC SUSCEPTIBILITY

(71) Applicant: NATIONAL INSTITUTE OF STANDARDS AND TECHNOLOGY, Gaithersburg, MD (US)

(72) Inventor: Daniel B. Gopman, Bethesda, MD (US)

(73) Assignee: The United States of America, as Represented by the Secretary of Commerce, Washington, DC (US)

( * ) Notice: Subject to any disclaimer, the term of this patent is extended or adjusted under 35 U.S.C. 154(b) by 6 days.

(21) Appl. No.: 15/059,824

(22) Filed: Mar. 3, 2016

(65) Prior Publication Data

US 2016/0274199 A1 Sep. 22, 2016

Related U.S. Application Data

(60) Provisional application No. 62/134,629, filed on Mar. 18, 2015.

(51) Int. Cl.
| | | |
|---|---|---|
| *G01N 27/76* | (2006.01) | |
| *G01R 33/16* | (2006.01) | |
| *G01N 27/72* | (2006.01) | |
| *G01R 33/565* | (2006.01) | |

(52) U.S. Cl.
CPC .............. *G01R 33/16* (2013.01); *G01N 27/72* (2013.01); *G01N 27/76* (2013.01); *G01R 33/56536* (2013.01); *G05B 2219/37124* (2013.01); *G05B 2219/37185* (2013.01)

(58) Field of Classification Search
CPC .. G01N 27/76; G01R 33/16; G01R 33/56536; H05H 1/3405; G05B 2219/37124; G05B 2219/37185; G05G 2009/04755
USPC .................... 324/51, 55, 200, 201, 204, 228
See application file for complete search history.

(56) References Cited

U.S. PATENT DOCUMENTS

| | | | | |
|---|---|---|---|---|
| 2015/0047976 A1* | 2/2015 | Setford | ................. | C12Q 1/006 204/403.01 |
| 2015/0096906 A1* | 4/2015 | Bain | ................. | G01N 27/3272 205/792 |
| 2015/0144507 A1* | 5/2015 | Bain | ................. | G01N 27/3272 205/792 |

* cited by examiner

*Primary Examiner* — Jermele M Hollington
*Assistant Examiner* — Raul Rios Russo
(74) *Attorney, Agent, or Firm* — Toby D. Hain

(57) ABSTRACT

A susceptometer includes: a substrate; a plurality of electrodes including: a first pair of electrodes disposed on the substrate; a second pair of electrodes disposed on the substrate, the second pair of electrodes arranged collinear with the first pair of electrodes to form a set of aligned electrodes; and a third pair of electrodes disposed on the substrate, the third pair of electrodes arranged noncollinearly with set of aligned electrodes; and a solenoid circumscribingly disposed around the electrodes to: receive the sample such that the solenoid is circumscribingly disposed around the sample; receive an alternating current and produce an primary magnetic field based on the alternating current; and subject the sample to the primary magnetic field.

20 Claims, 32 Drawing Sheets

SUSCEPTOMETER AND PROCESS FOR DETERMINING MAGNETIC SUSCEPTIBILITY

CROSS REFERENCE TO RELATED APPLICATIONS

This application claims the benefit of U.S. Provisional Patent Application Ser. No. 62/134,629 filed Mar. 18, 2015, the disclosure of which is incorporated herein by reference in its entirety.

STATEMENT REGARDING FEDERALLY SPONSORED RESEARCH

This invention was made with United States Government support from the National Institute of Standards and Technology. The Government has certain rights in the invention.

BRIEF DESCRIPTION

Disclosed is a susceptometer comprising: a substrate; a plurality of electrodes to: subject a sample to a direct current electrical current; and measure at least one of a Hall voltage of the sample or a current-in-plane resistance of the sample, the plurality of electrodes comprising: a first pair of electrodes disposed on the substrate and being electrically conductive to engage and be in electrical contact with a sample; a second pair of electrodes disposed on the substrate and being electrically conductive to engage and be in electrical contact with the sample, the second pair of electrodes arranged collinear with the first pair of electrodes to form a set of aligned electrodes; and a third pair of electrodes disposed on the substrate and being electrically conductive to engage and be in electrical contact with the sample, the third pair of electrodes arranged noncollinearly with set of aligned electrodes; and a solenoid circumscribingly disposed around the electrodes to: receive the sample such that the solenoid is circumscribingly disposed around the sample; receive an alternating current and produce a primary magnetic field based on the alternating current; and subject the sample to the primary magnetic field.

Further disclosed is a susceptometer to perform magnetic susceptometry on a sample, the susceptometer comprising: a chamber; a substrate disposed in the chamber; a plurality of electrodes disposed in the chamber and being electrically reconfigurable in-situ and in contact with the sample to obtain reconfigurably the Hall voltage of the sample and the current-in-plane resistance of the sample and to subject the sample to a direct current electrical current, the plurality of electrodes comprising: a first pair of electrodes disposed on the substrate and being electrically conductive to engage and be in electrical contact with a sample; a second pair of electrodes disposed on the substrate and being electrically conductive to engage and be in electrical contact with the sample, the second pair of electrodes arranged collinear with the first pair of electrodes to form a set of aligned electrodes; and a third pair of electrodes disposed on the substrate and being electrically conductive to engage and be in electrical contact with the sample, the third pair of electrodes arranged noncollinearly with set of aligned electrodes; and a fourth pair of electrodes disposed on the substrate and being electrically conductive to engage and be in electrical contact with the sample, the fourth pair of electrodes arranged noncollinearly with set of aligned electrodes and arranged in a square pattern with the third pair of electrodes; and a solenoid disposed in the chamber and circumscribingly disposed around the electrodes to: receive the sample such that the solenoid is circumscribingly disposed around the sample; receive an alternating current and produce an primary magnetic field based on the alternating current; and subject the sample to the primary magnetic field Disclosed also is a process for performing magnetic susceptometry on a sample, the process comprising: providing the sample to a susceptometer comprising: a substrate; a plurality of electrodes comprising: a first pair of electrodes disposed on the substrate and being electrically conductive to engage and be in electrical contact with a sample; a second pair of electrodes disposed on the substrate and being electrically conductive to engage and be in electrical contact with the sample, the second pair of electrodes arranged collinear with the first pair of electrodes to form a set of aligned electrodes; and a third pair of electrodes disposed on the substrate and being electrically conductive to engage and be in electrical contact with the sample, the third pair of electrodes arranged noncollinearly with set of aligned electrodes; and a solenoid circumscribingly disposed around the electrodes; receiving the sample in the solenoid such that the solenoid is circumscribingly disposed around the sample; providing the solenoid with an alternating current; producing, by the solenoid, a primary magnetic field in response to receiving the alternating current; subjecting the sample to the primary magnetic field; and subjecting the sample to a direct current electrical current to perform magnetic susceptometry.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

It has been discovered that a susceptometer can perform magnetic susceptibility measurements of a sample, e.g., a thin semiconducting or a ferromagnetic film. The susceptometer can generate an alternating magnetic field and subject the sample to the alternating magnetic field. Advantageously, the susceptometer provides measurement of a steady state (i.e., direct current DC) voltage response (U) of the sample subjected to a secondary magnetic field or a differential voltage response (ΔU) to the alternating magnetic field provided by a solenoid (e.g., a primary magnetic field that has an excitation field (ΔB) and a frequency f).

Figure 1:
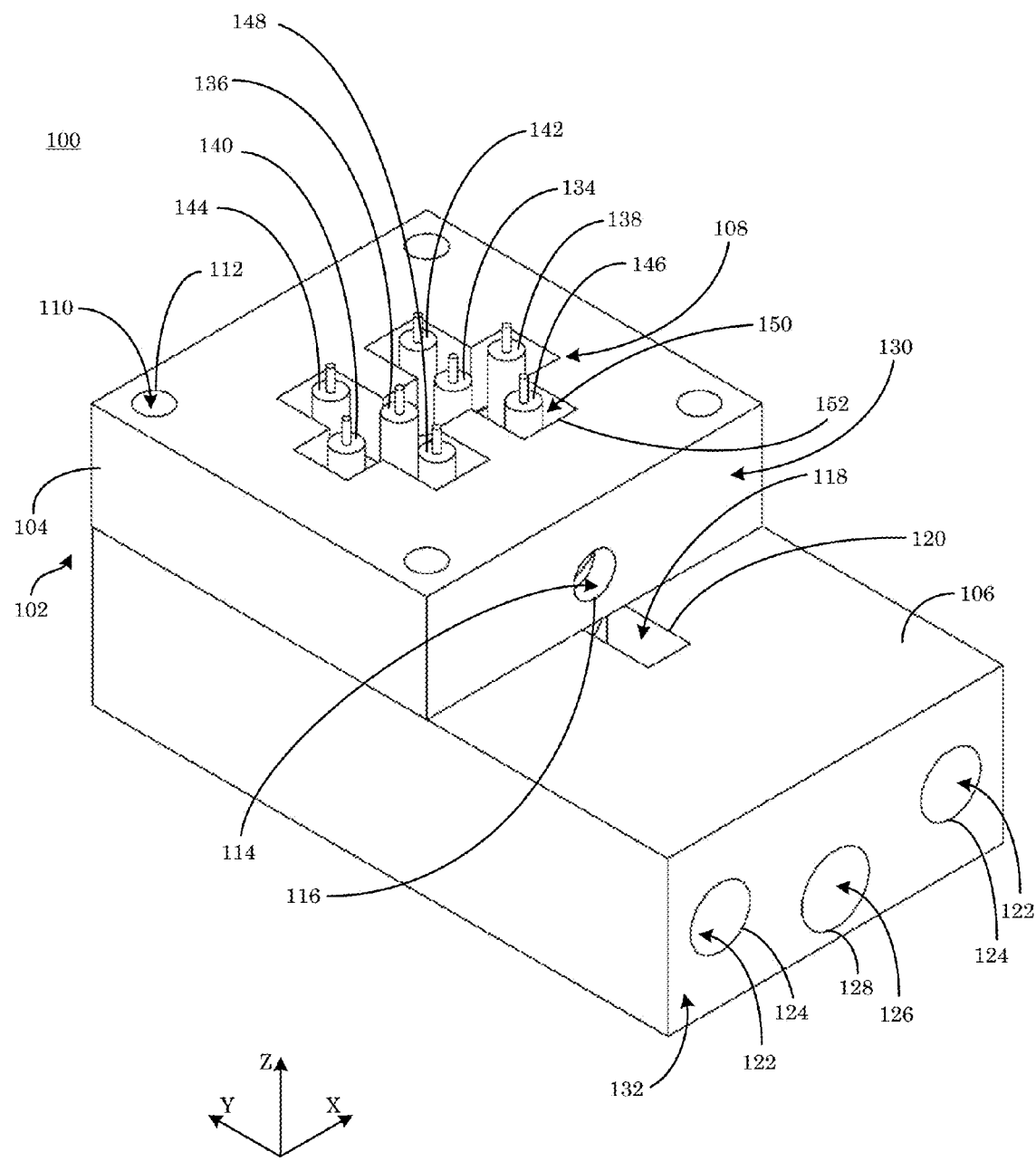
FIG. 1 shows a perspective view of a susceptometer.
Figure 2:
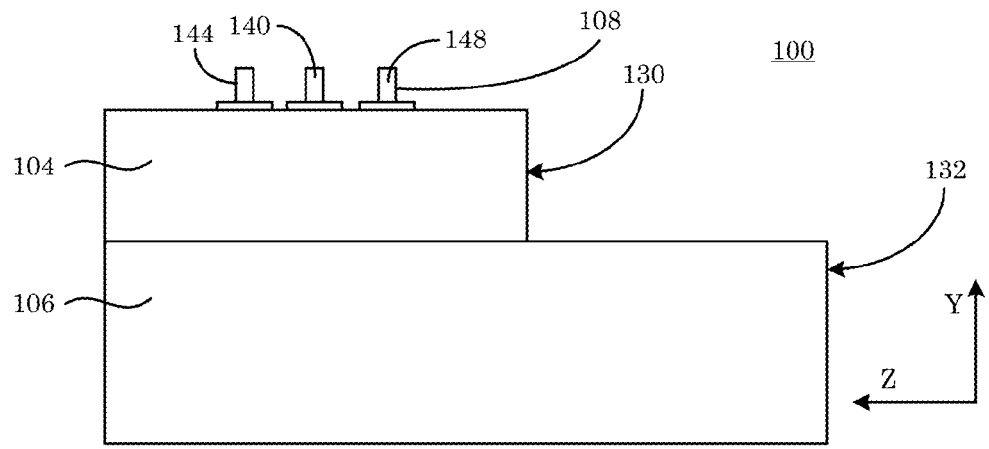
FIG. 2 shows a side view of the susceptometer shown in FIG. 1.
Figure 3:
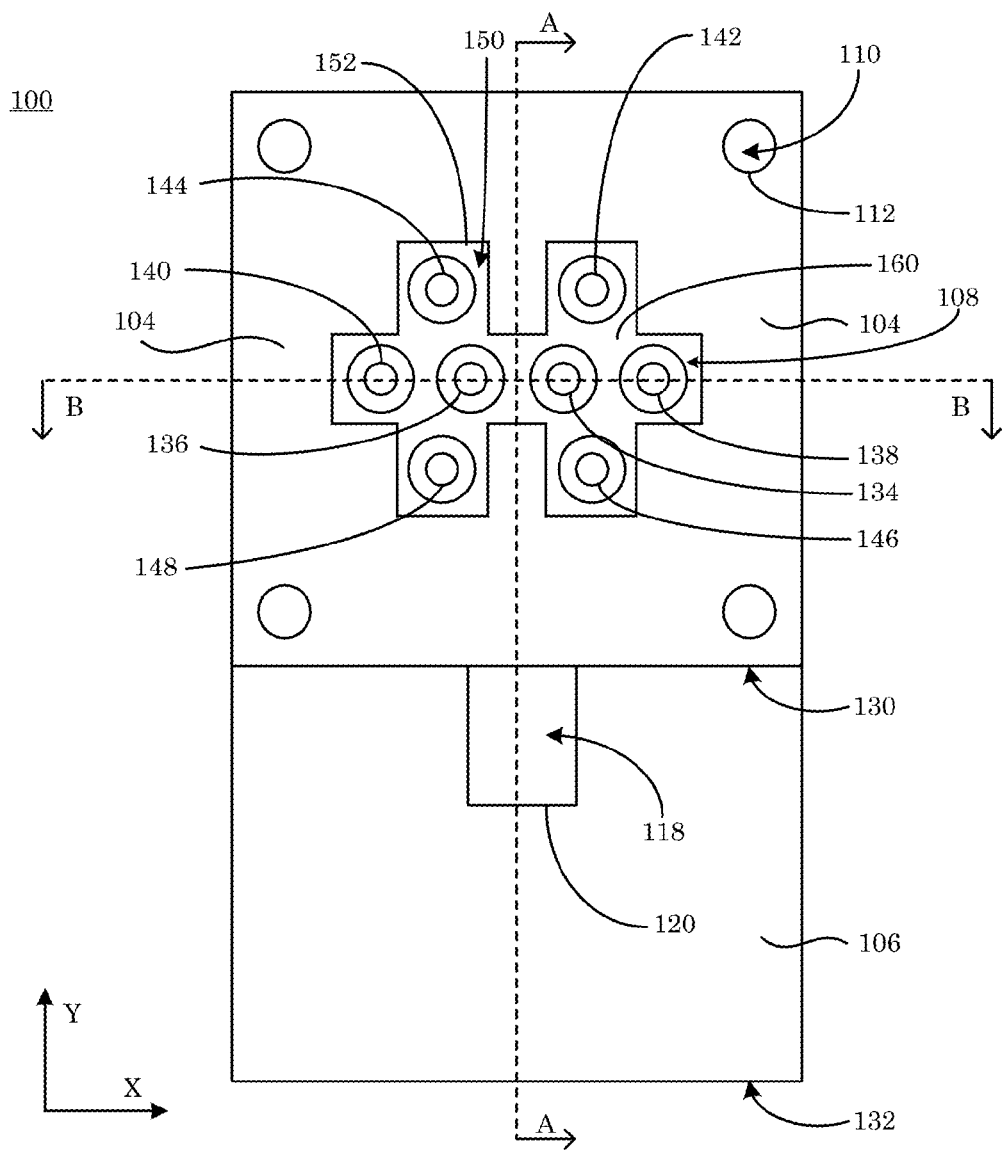
FIG. 3 shows a top view of the susceptometer shown in FIG. 1.
Figure 4:
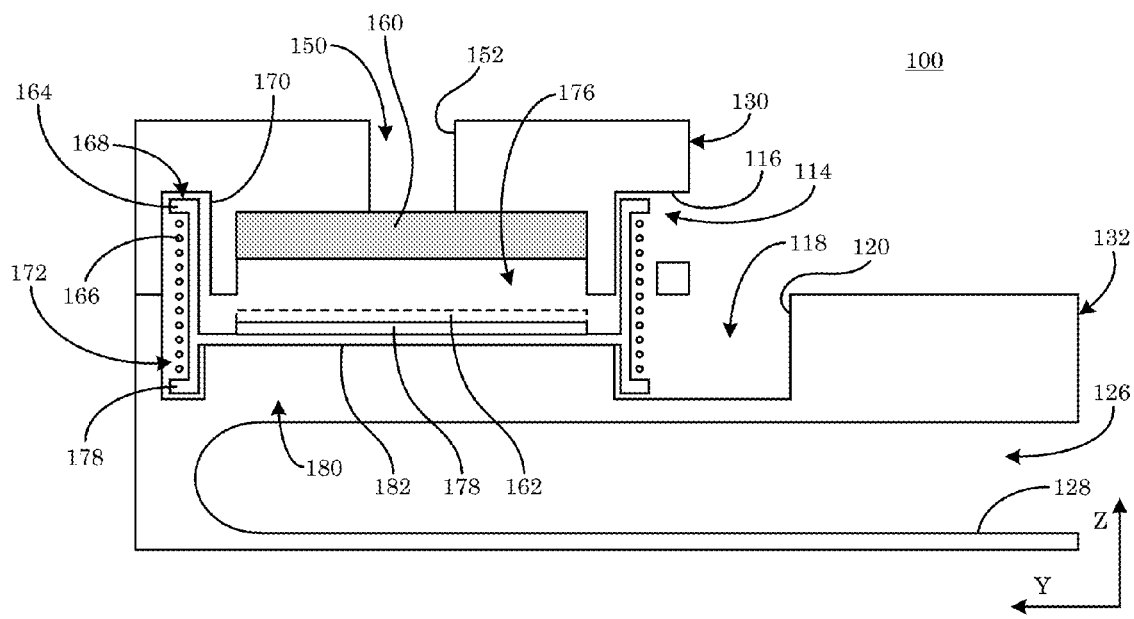
FIG. 4 shows a cross-section along line A-A of the susceptometer shown in FIG. 3.
Figure 5:
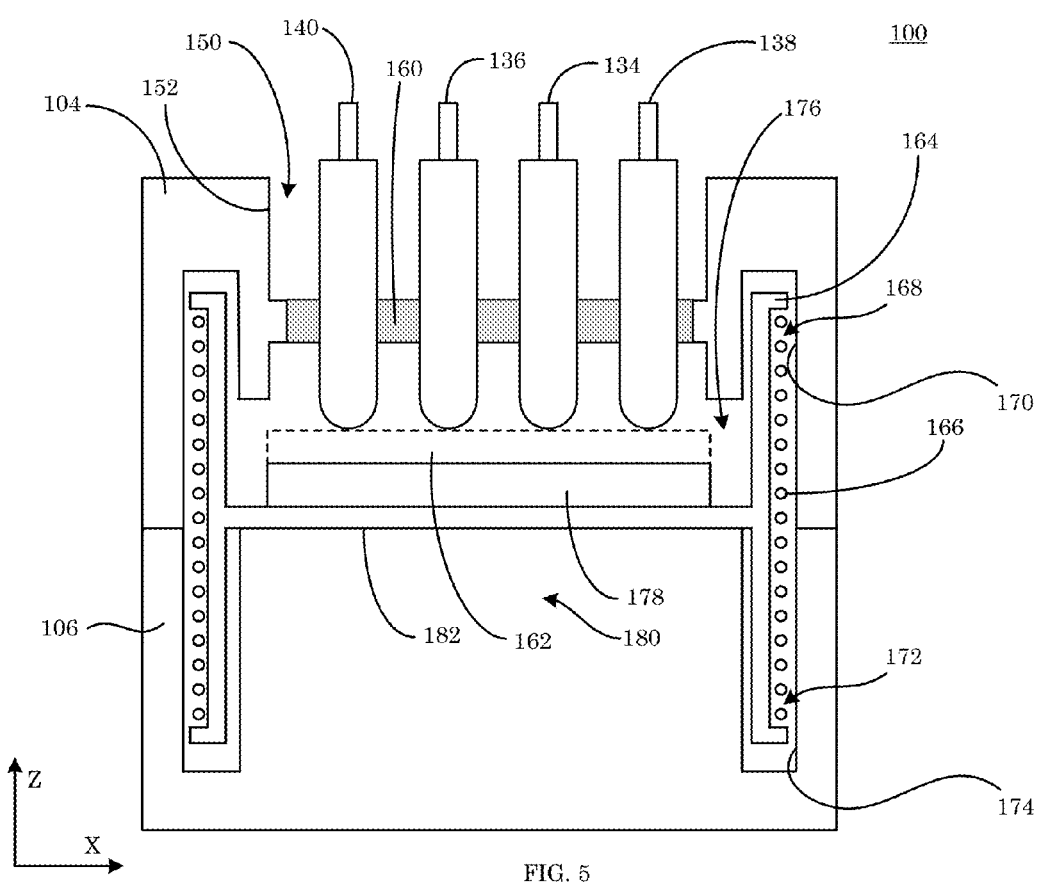
FIG. 5 shows a cross-section along line B-B of the susceptometer shown in FIG. 3.

In an embodiment, with reference to FIG. 1 (perspective view of susceptometer 100), FIG. 2 (side view of susceptometer 100), FIG. 3 (top view of susceptometer 100), FIG. 4 (cross-section along line A-A of susceptometer 100 shown in FIG. 2), FIG. 5 (cross-section along line B-B of susceptometer 100 shown in FIG. 2), susceptometer 100 includes chamber 102 and a plurality of electrodes 108. Chamber 102 includes electrode chamber 104 and sample chamber 106. Electrodes 108 are disposed in electrode chamber 104. Electrodes 108 include, e.g., electrodes 134, 136, 138, 140, 142, 144, 146, and 148. More electrodes than shown can be included in susceptometer 100. In some embodiments, some of electrodes (134, 136, 138, 140, 142, 144, 146) are absent. Electrode chamber 104 optionally can include various apertures (e.g., 110 or 114) that can be bounded by wall (e.g., 112 or 116). Aperture 110 can receive a fastener to fasten electrode chamber 104 to sample chamber 106. Exemplary fasteners include a screw, bolt, pin (e.g., cotter pin), adhesive, and the like. Aperture 114 bounded by wall 114 disposed in first end 130 of electrode chamber 106 receives an electrical wire to connect to an internal component (i.e., a component disposed in chamber 102 such as a solenoid), a flow line (e.g., a cooling or heating line), and the like. Additionally, sample chamber 104 includes electrode aperture 150 bounded by wall 152 to provide clearance for electrodes 108 (e.g., 134, 136, 140, 138, 144, 142, 140, 146). In this manner, electrodes 108 are electrically isolated from wall 152.

Aperture 118 bounded by wall 120 and disposed in first end 132 of sample chamber 106 receives an electrical wire to connect to an internal component (i.e., a component disposed in chamber 102 such as a solenoid), a flow line (e.g., a cooling or heating line), and the like. Sample chamber 106 also includes aperture 126 bounded by wall 128, which can receive, e.g., a heater (not shown) or another temperature control device such as a cold finger, Peltier junction, and the like to control a temperature of a sample disposed in sample chamber 106. Aperture 122 bounded by wall 124 is disposed in sample chamber 106 to receive a coupler (not shown) couple susceptometer 100 to a mount (not shown, but see FIG. 7, e.g., mount).

As shown in FIG. 4 and FIG. 5, electrodes 108 (including electrodes 134, 136, 138, 140, 142, 144, 146, 148) are disposed in substrate 160. Substrate 160 electrically isolates electrodes 108 from electrode chamber 104. Electrode chamber 104 disposed in contact with sample chamber 106 form sample cavity 176 that is a void in which sample platform 178 is disposed inside of chamber 102. Sample platform 178 supports sample 162, and platform 178 is disposed on surface 182 of platform 180 of sample chamber 106. In this manner, sample chamber 106 receives sample platform 178. Solenoid 166 is disposed in a coil around spool 164. Spool 164 is disposed in sample cavity 176 and received in solenoid receiver 168 bounded by wall 170 of electrode chamber 104 and also received in solenoid receiver 172 bounded by wall 174 of sample chamber 106. Accordingly, sample 162 disposed on sample platform 178 is disposed in chamber 102 of susceptometer 100. It should be appreciated that electrodes 108 (e.g., electrodes 140, 136, 134, 138, and the like) electrically contact sample 162 inside sample cavity 176.

Figure 6:
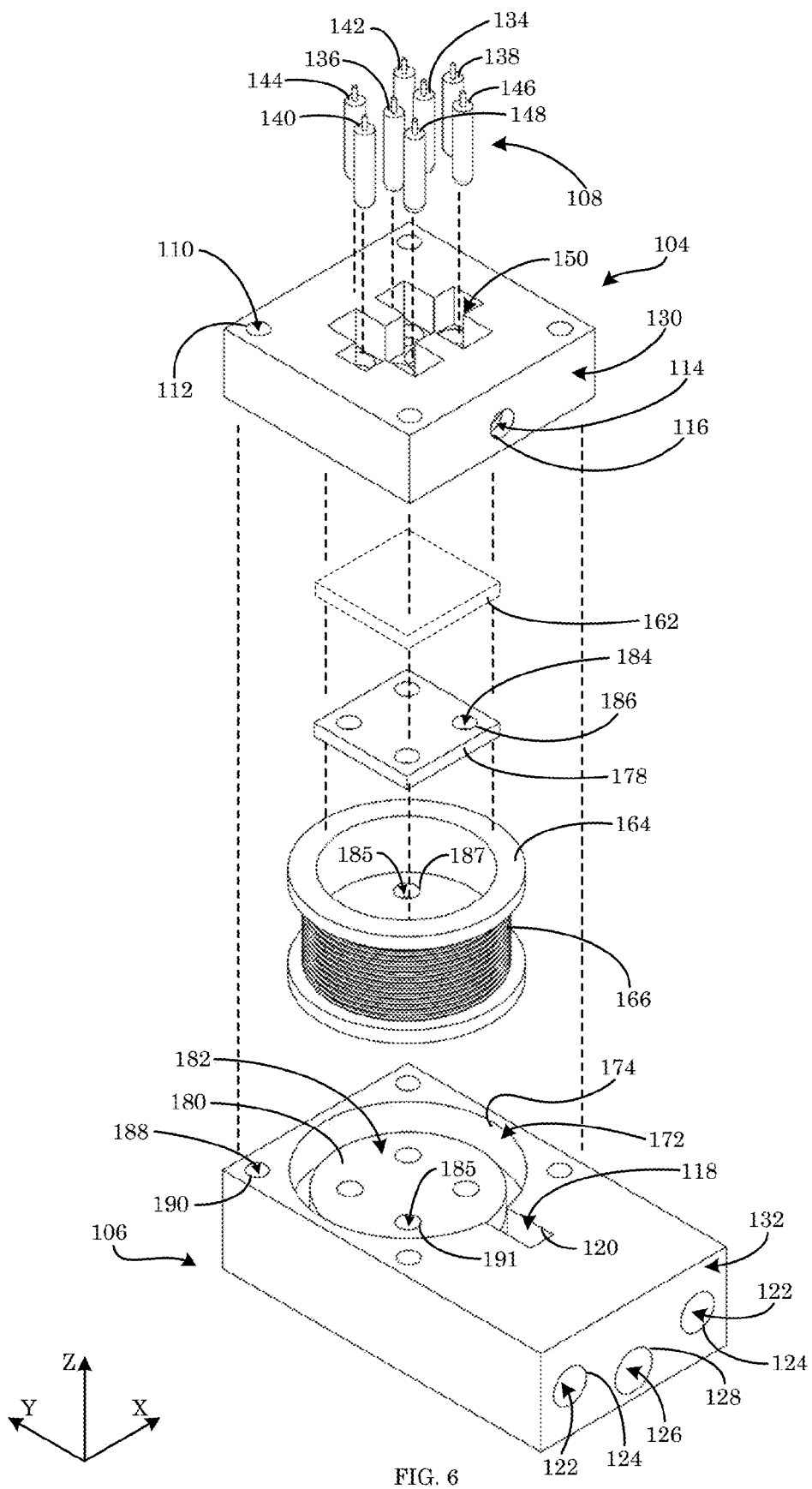
FIG. 6 shows an exploded view of the susceptometer shown in FIG. 1.

An exploded view of susceptometer 100 is shown in FIG. 6 in which electrodes 108 are disposed in substrate 160 that is disposed in electrode chamber 104. Further, sample platform 178 is disposed in spool 164 that is received by sample chamber 106. Here, sample chamber 106 includes aperture 188 bounded by wall 190 to receive the fastener received by aperture 110 of electrode chamber 104, and wall 190 engages the fastener to fasten electrode chamber 104 to sample chamber 106. Additionally, sample chamber 106 includes aperture 189 bounded by wall 191 disposed in platform 180 to receive a fastener inserted there in to fasten spool 164 and sample platform 178 two surface 182 of platform 180. Sample 162 can be attached to sample platform 178, e.g., with a fastener, adhesive, and the like. In an embodiment, sample 162 is formed (e.g., grown) on sample platform 178.

Figure 7:
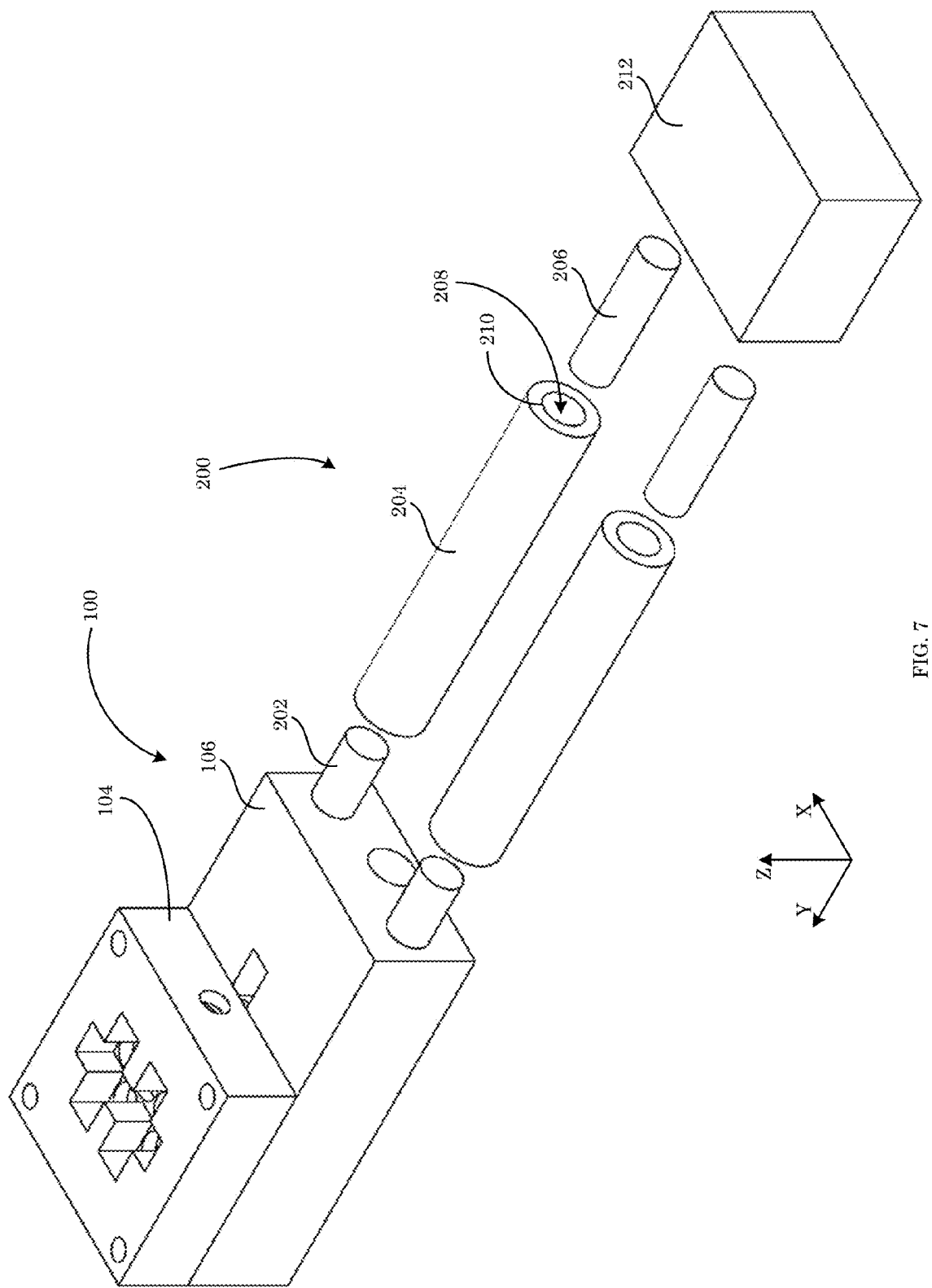
FIG. 7 shows a perspective view of the susceptometer shown in FIG. 1 disposed on amount.

In an embodiment, as shown in FIG. 7, susceptometer 100 can be disposed on mount 200 to mount susceptometer 100. Mount 200 can include couplers 202, 204, 206 to couple susceptometer 100 to receiver 212. Coupler 202 can be inserted into aperture 122 of sample chamber 106 of susceptometer 100. Wall 124 that bounds aperture 122 can engage coupler 202. Coupler 204 can include aperture 208 bounded by wall 210 such that after 208 receives coupler 202 and coupler 206 that opposing ends of coupler 204. Receiver 212 can include an aperture (not shown) to receive coupler 206. Receiver 212 can be a stationary mount or maneuverable and can further couple susceptometer 100 to a member for manipulating a position of susceptometer 100 or to fix a location of susceptometer 100.

Figure 8:
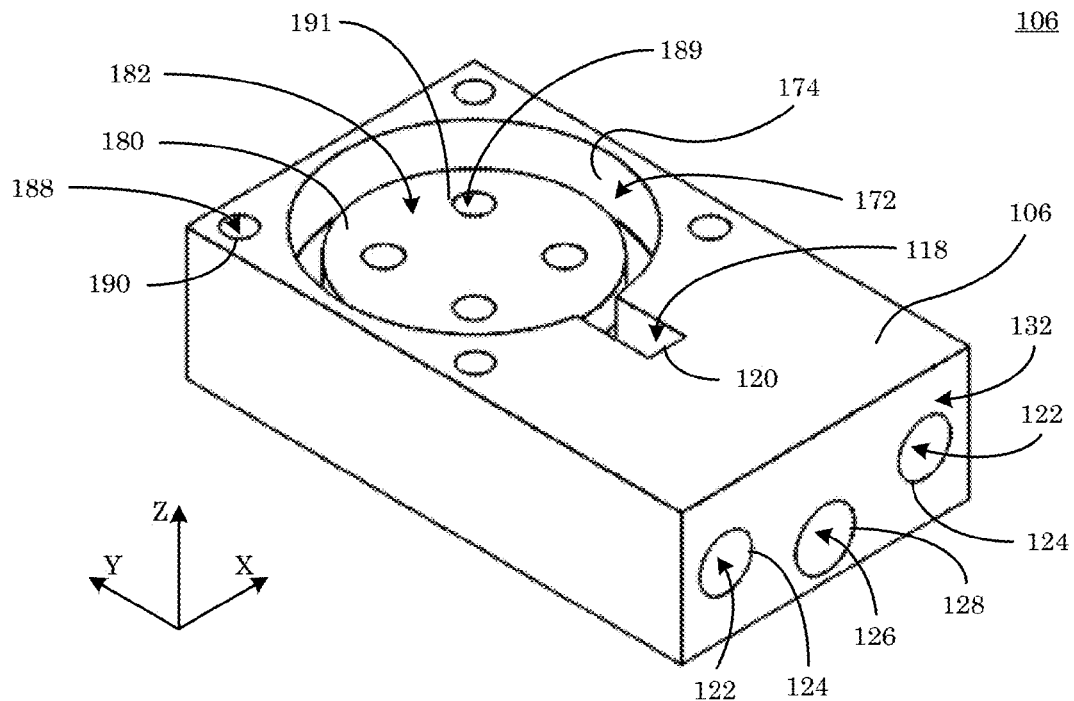
FIG. 8 shows a perspective view of the sample chamber shown in FIG. 1.
Figure 9:
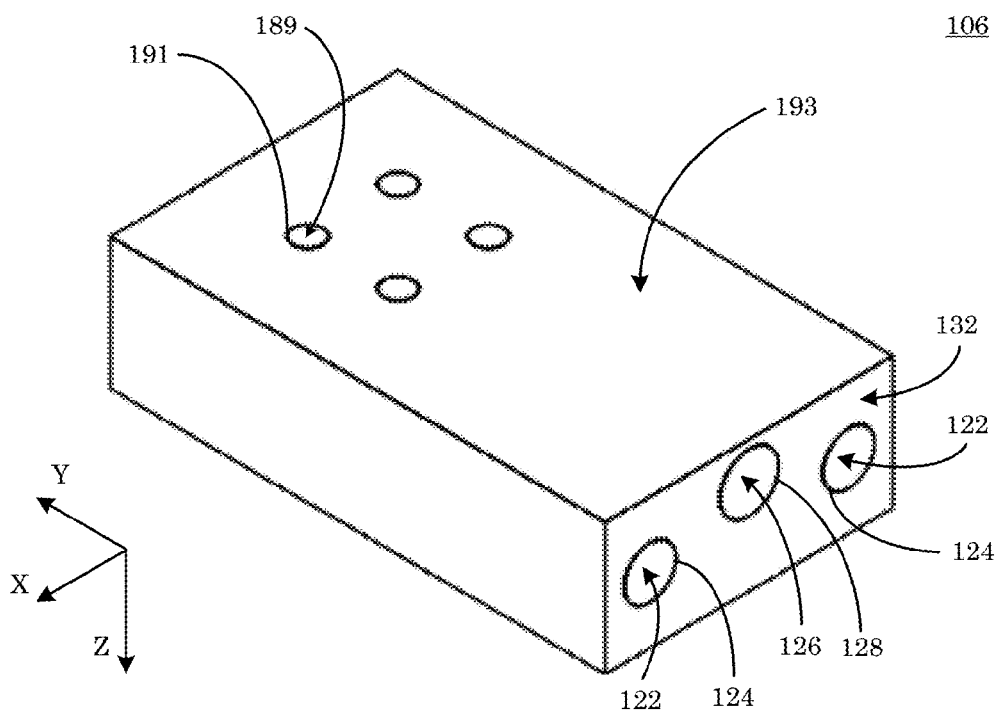
FIG. 9 shows a perspective view of the sample chamber shown in FIG. 1.
Figure 10:
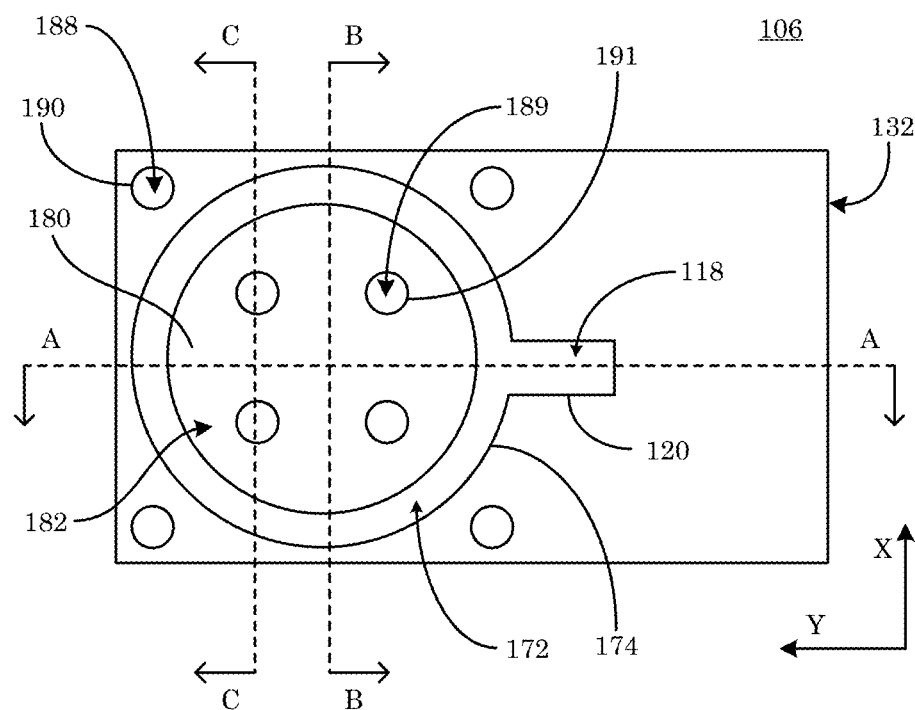
FIG. 10 shows a top view of the sample chamber shown in FIG. 1.
Figure 11:
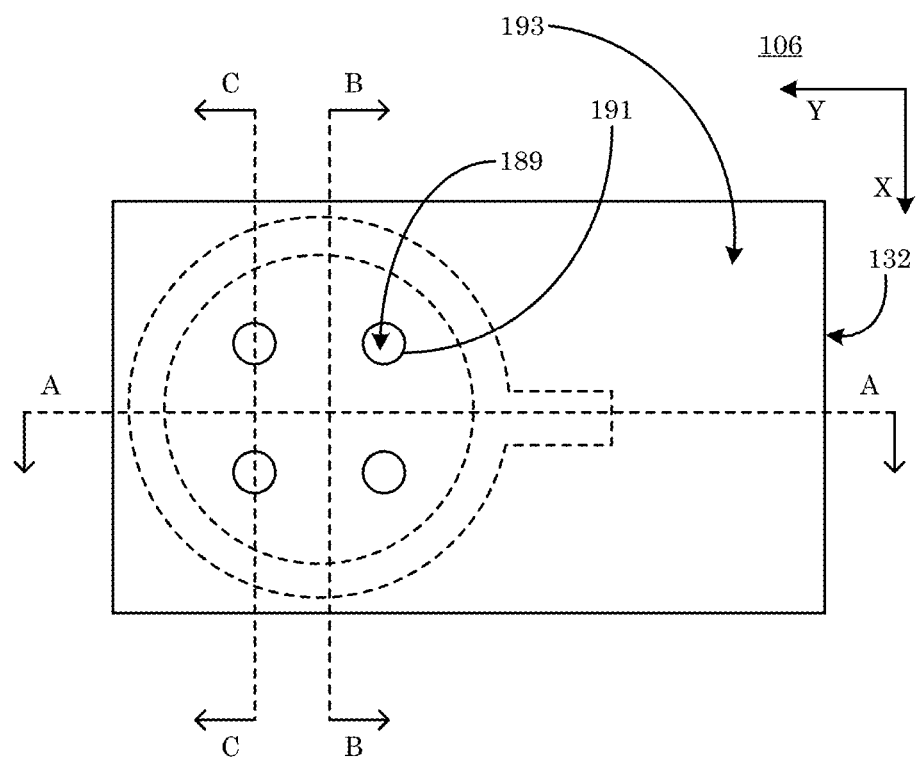
FIG. 11 shows a bottom view of the sample chamber shown in FIG. 1.
Figure 12:
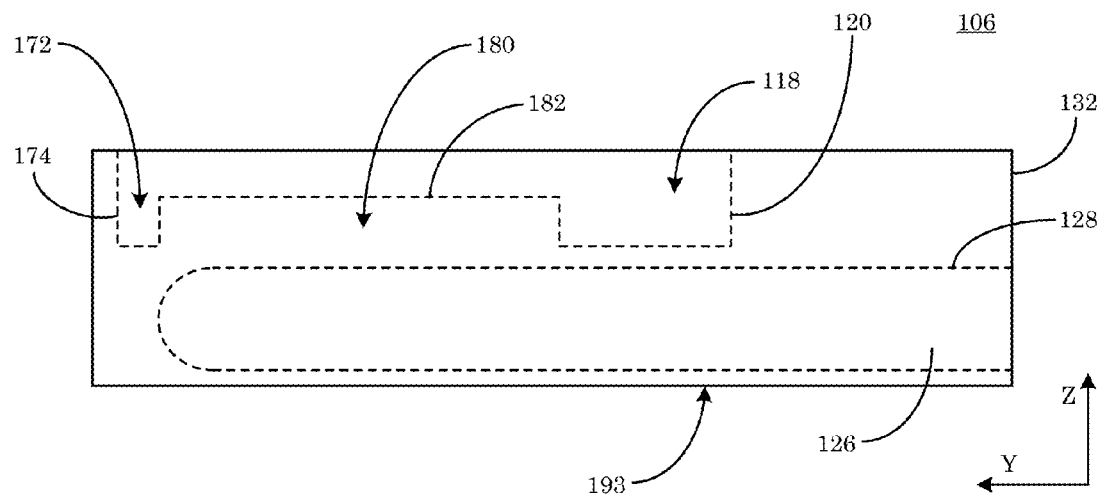
FIG. 12 shows a side view of the sample chamber shown in FIG. 1.
Figure 13:
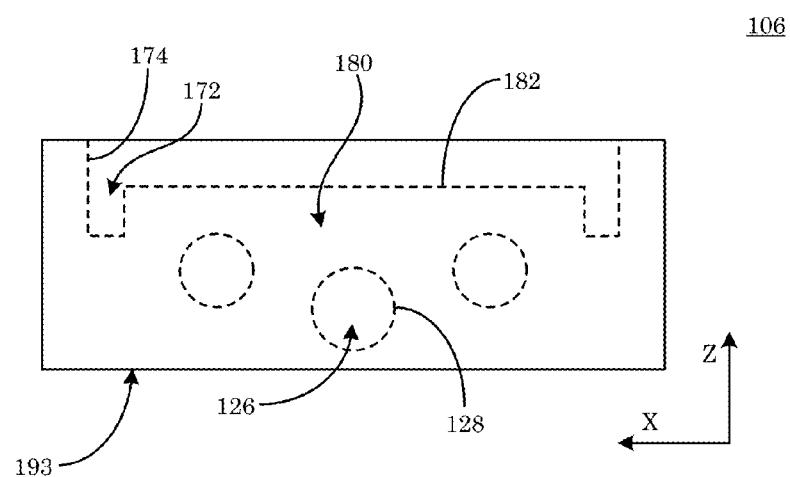
FIG. 13 shows an end view of the sample chamber shown in FIG. 1.
Figure 14:
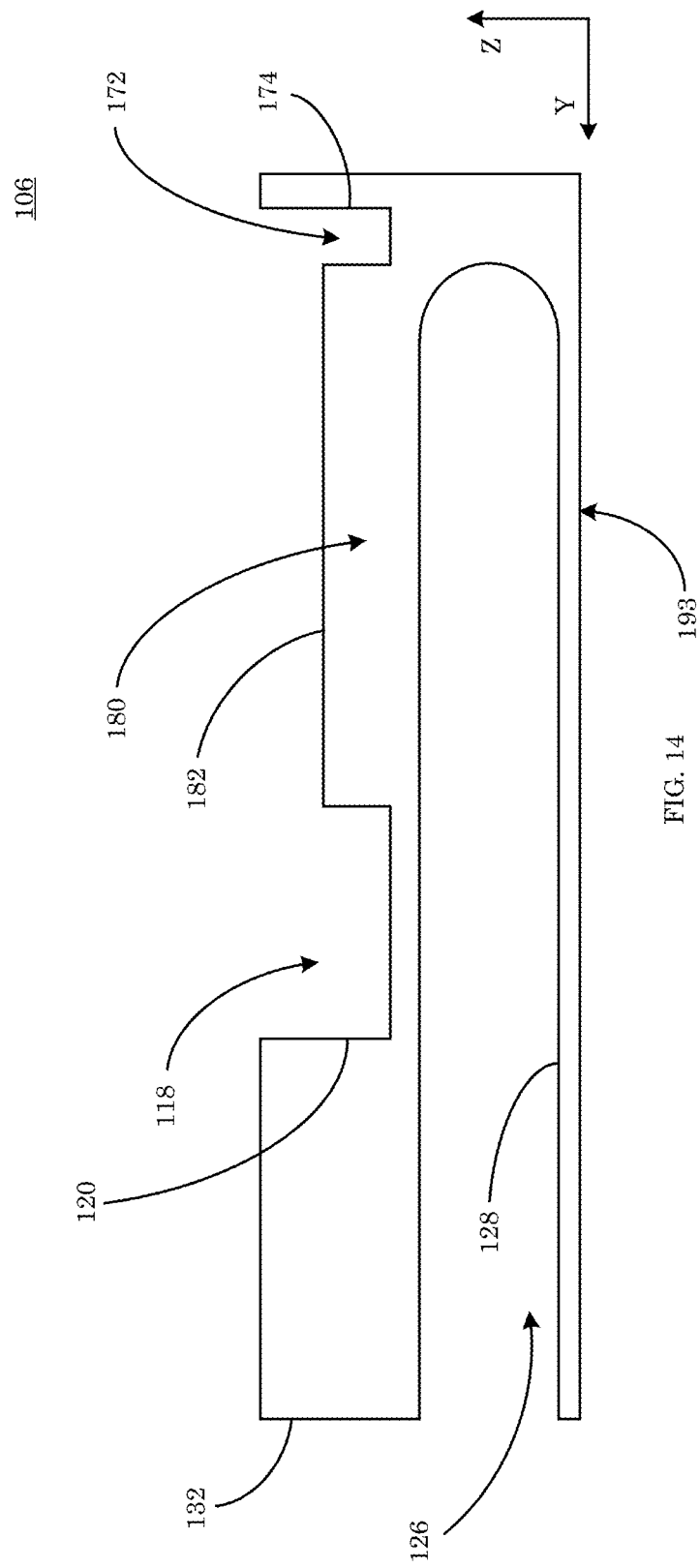
FIG. 14 shows a cross-section along line A-A of the sample chamber shown in FIG. 10.
Figure 15:
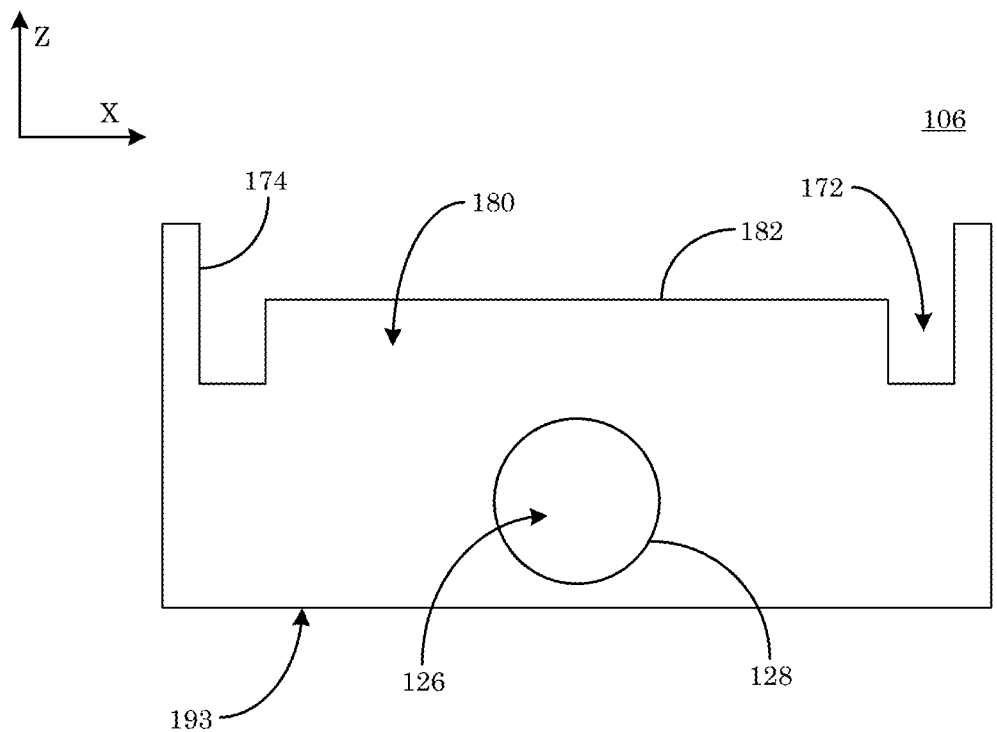
FIG. 15 shows a cross-section along line B-B of the sample chamber shown in FIG. 10.
Figure 16:
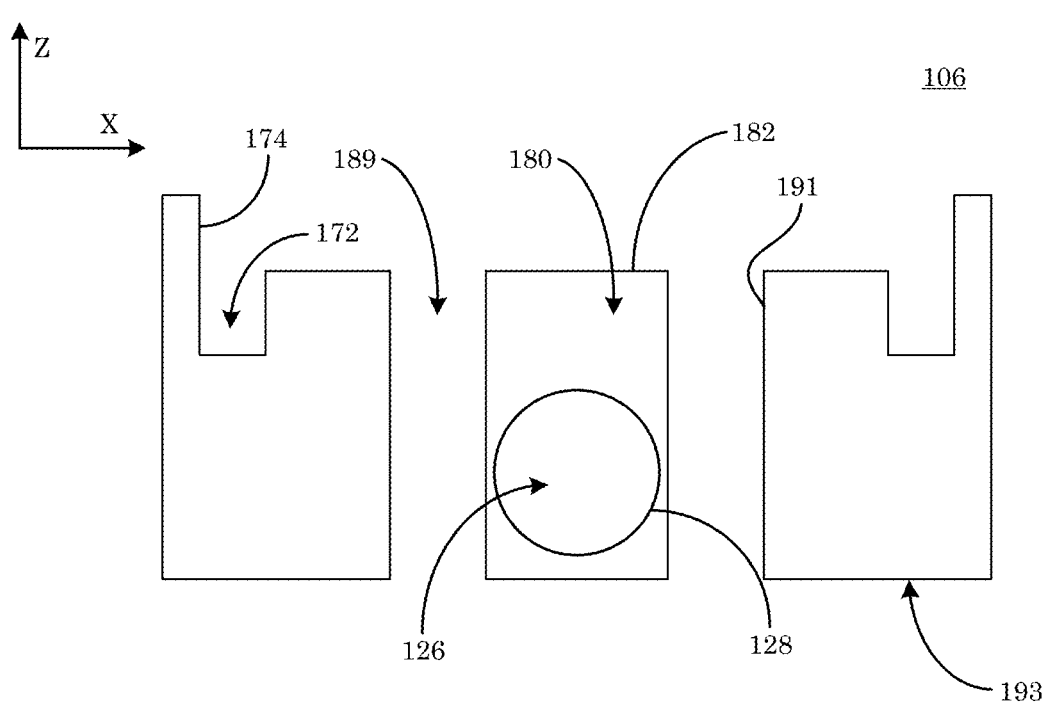
FIG. 16 shows a cross-section along line C-C of the sample chamber shown in FIG. 10.
Figure 17:
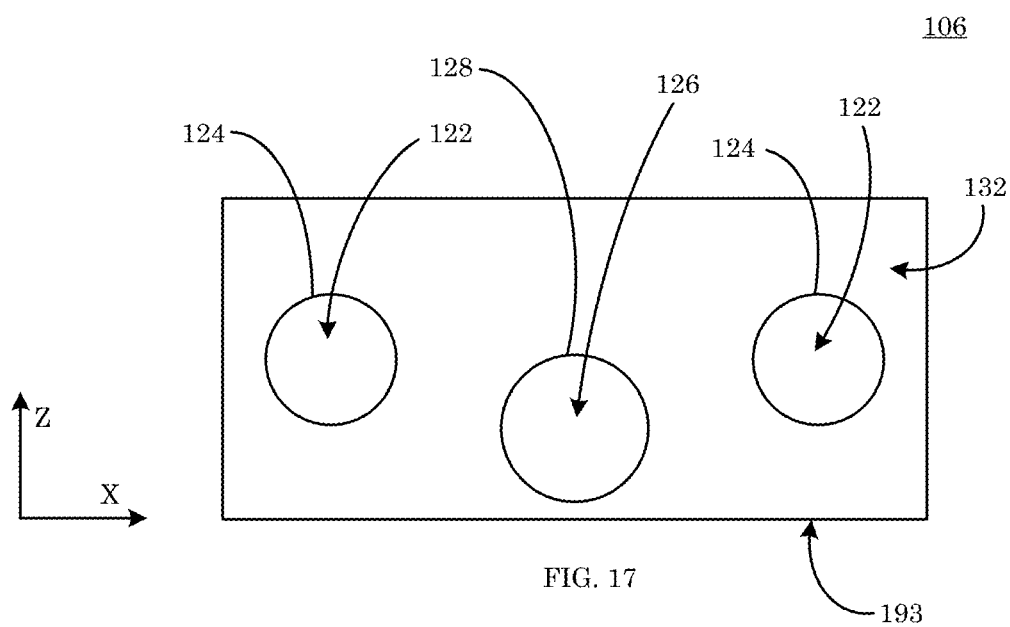
FIG. 17 shows an end view of the sample chamber shown in FIG. 10.

According to an embodiment, susceptometer 100 includes sample chamber 106 that, in combination with electrode chamber 104, provides sample cavity 176 to receive sample 162, spool 164, and solenoid 166 disposed on spool 164. Here, sample chamber 106 is shown in FIG. 8 (top perspective view of sample chamber 106), FIG. 9 (bottom perspective view of sample chamber 106), FIG. 10 (top view of sample chamber 106), FIG. 11 (bottom view of sample chamber 106), FIG. 12 (side view of sample chamber 106), FIG. 13 (end view of sample chamber 106 along Y-Axis), FIG. 14 (cross-section along line A-A shown in FIG. 10), FIG. 15 (cross-section along line B-B shown in FIG. 10), FIG. 16 (cross-section along line C-C shown in FIG. 10), FIG. 17 (end view of sample chamber 106). Aperture 188 bounded by wall 190 disposed in sample chamber 106 receives the fastener provided through aperture 110 bounded by 112 disposed in electrode chamber 104. Wall 190 engages the fastener to fasten sample chamber 106 to electrode chamber 104. Electrode chamber 104 also includes platform 180 that includes surface 182 to receive sample 162, spool 164, and sample platform 178. Aperture 189 bounded by wall 191 is disposed in platform 180 to receive a fastener that wall 191 engages to fasten sample 162, spool 164, and sample platform 178 to platform 180. Aperture 189 can be a through hole that traverses platform 180 from bottom surface 193 shown in FIG. 9 to surface 182 shown in FIG. 8. As shown in FIG. 9, the fastener can be inserted into aperture 189 at bottom surface 193, communicated through aperture 189 to surface 182, and communicated and engaged by sample platform 178, spool 164, and optionally sample 162. It is contemplated that wall 191 of aperture 189 of sample chamber 106 and wall 187 of spool 164 can be through holes while wall 186 bounding aperture 184 of sample platform 178 is threaded to receivingly engage the fastener. In sample chamber 106 platform 180 is surrounded by solenoid receiver 172 that is bounded by wall 174. Solenoid receiver 172 receives spool 164. Solenoid receiver 172 is in communication with aperture 118 bounded by wall 120. In this manner, a wire can be disposed in and received by aperture 118 such that solenoid 166 disposed on spool 164 that is received by solenoid receiver 172 is connected to the wire when sample chamber 106 is contacted by electrode chamber 104. The wire provides electrical communication to solenoid 166 even though solenoid 166 is not exposed beyond sample cavity 176 formed and enclosed by sample chamber 106 and electrode chamber 104.

In an embodiment, a temperature of platform 180 is controlled by a thermal member (not shown) disposed in aperture 126 bounded by wall 128 that traverses sample chamber 106 from first end 132. The thermal member can be a heater cartridge, Peltier junction, fluid pipe, and the like. The thermal member can heat or cool platform 180. Platform 180 is in thermal contact with spool 164 disposed at surface 182 of platform 180. Moreover, spool 164 is in thermal contact with sample platform 178, which is in thermal contact with sample 162. According to an embodiment, a temperature of sample 162 can be substantially similar or identical to the temperature of platform 180, at surface 182 of sample chamber 106. Because of the thermal contact between sample 162 and platform 180, the thermal member controls a temperature of platform 180 and sample 162.

Sample chamber 106 also can include aperture 122 bounded by wall 124 to mount and control a position or motion of sample electrode 106. Wall 124 can be a through hole (e.g., to receive coupler 202 that is press fit therein), tapped (e.g., to receive coupler 202 that is screwed into aperture 122), and the like. In this manner, wall 124 engages coupler 202.

Figure 18:
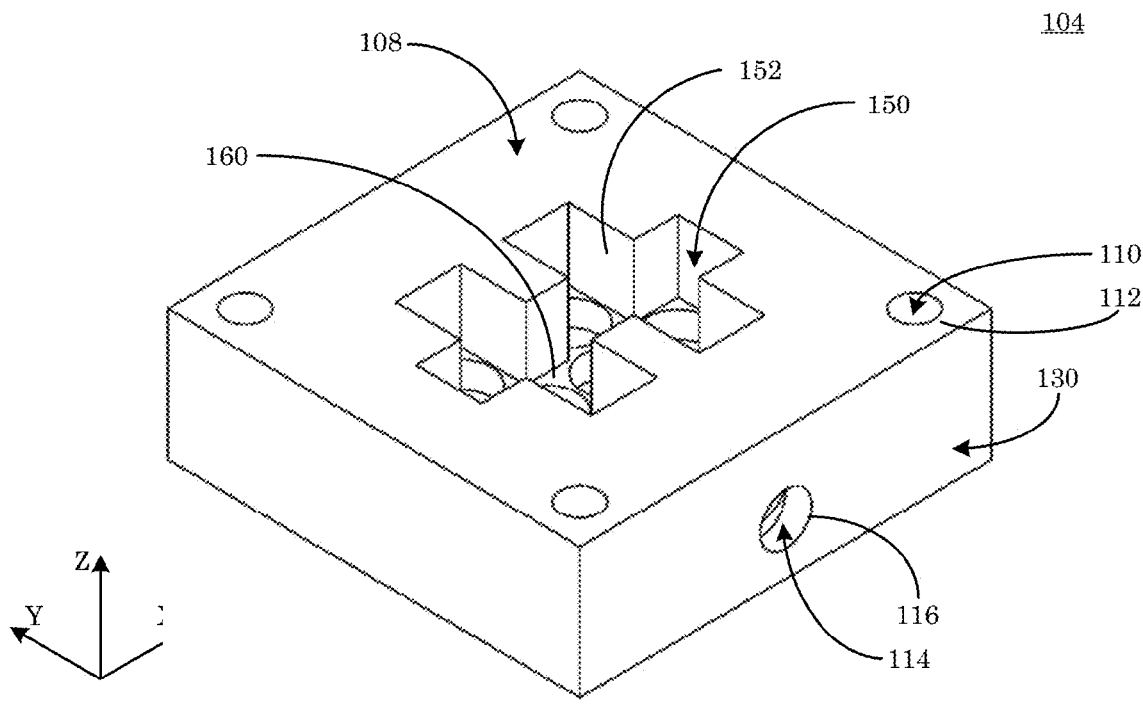
FIG. 18 shows a top perspective view of the electrode chamber shown in FIG. 1.
Figure 19:
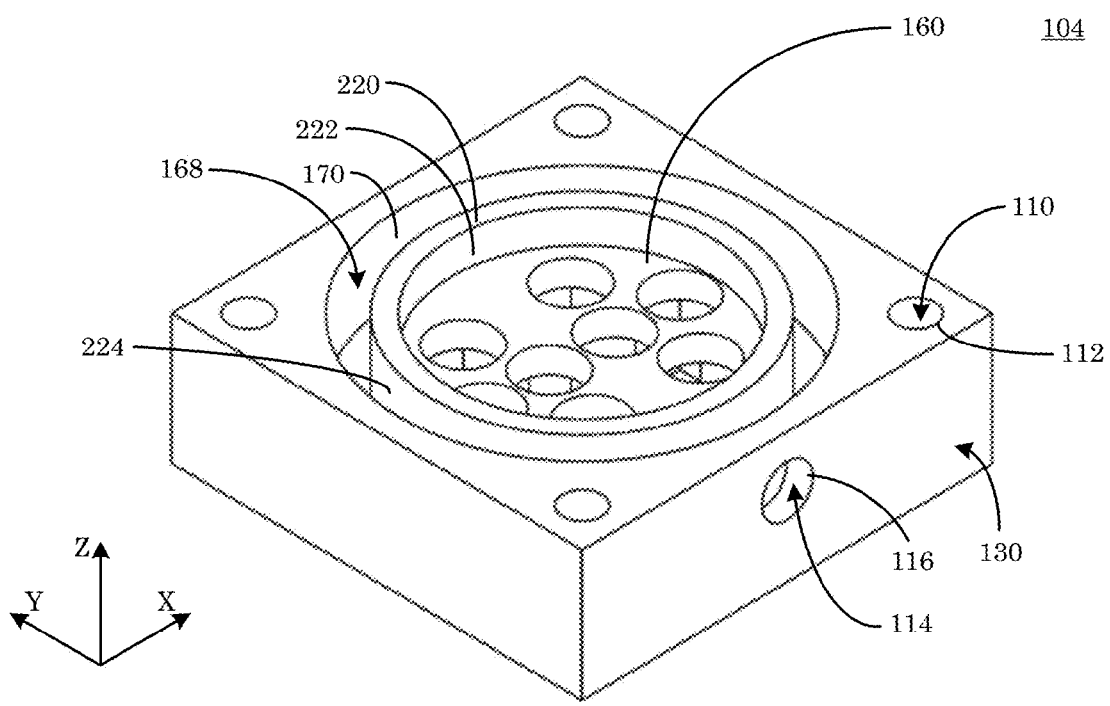
FIG. 19 shows a bottom perspective view of the electrode chamber shown in FIG. 1.
Figure 20:
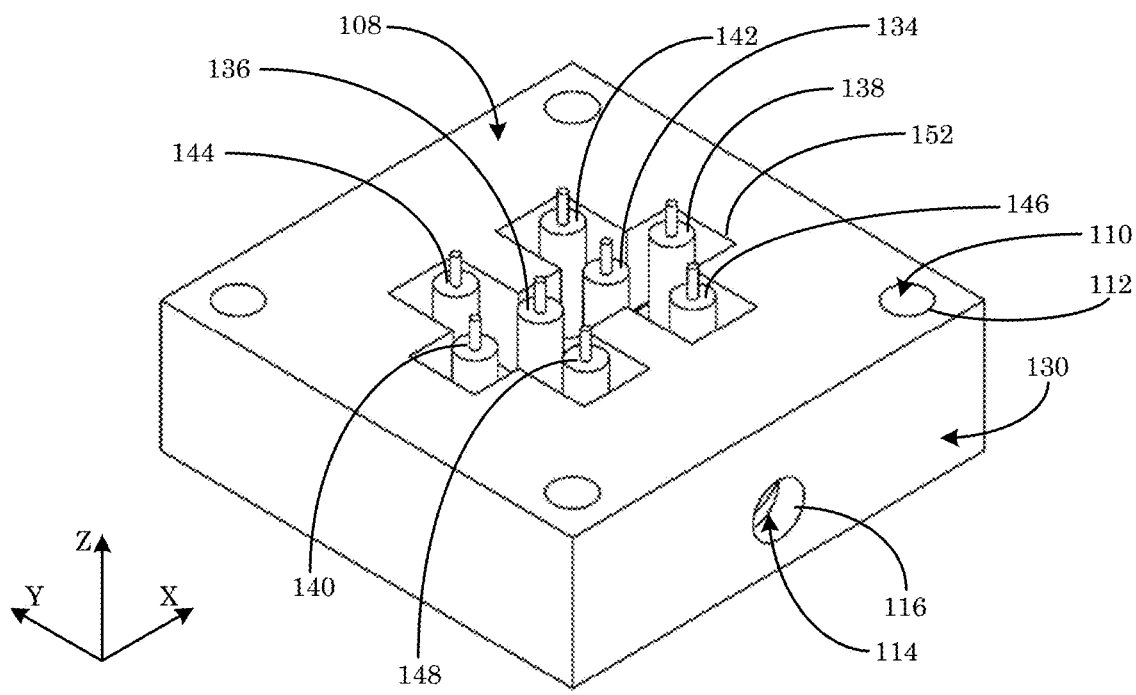
FIG. 20 shows a top perspective view of the electrode chamber shown in FIG. 18.
Figure 21:
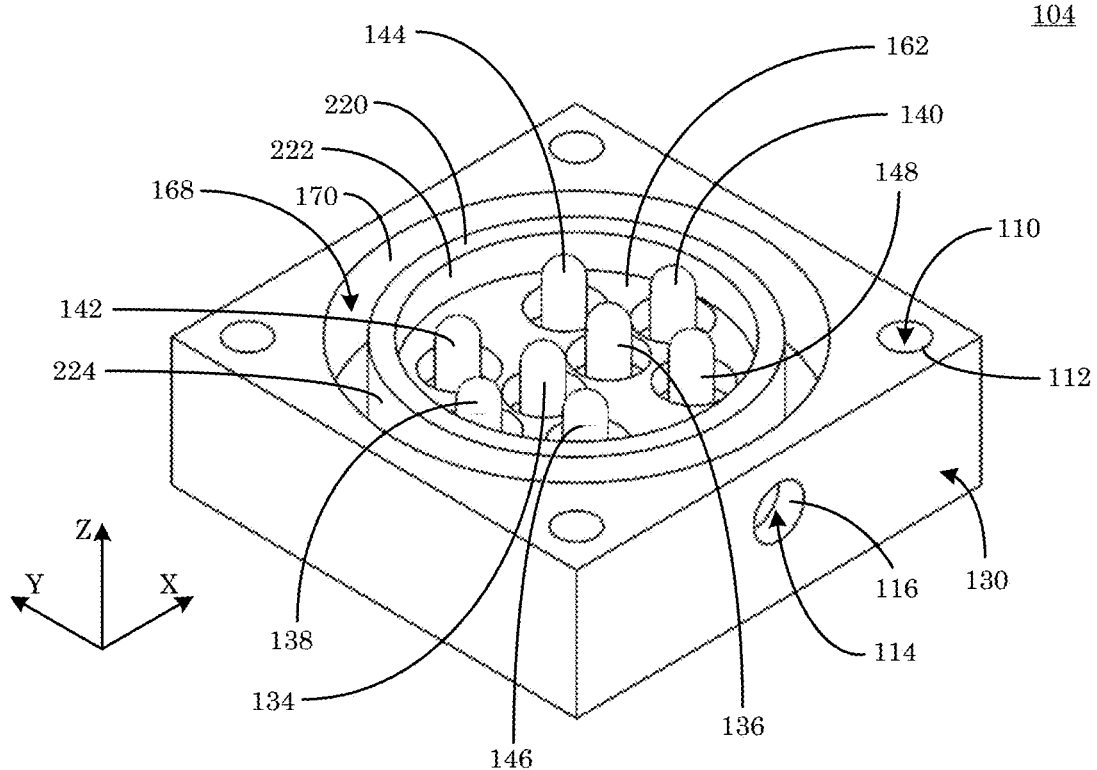
FIG. 21 shows a bottom perspective view of the electrode chamber shown in FIG. 19.
Figure 22:
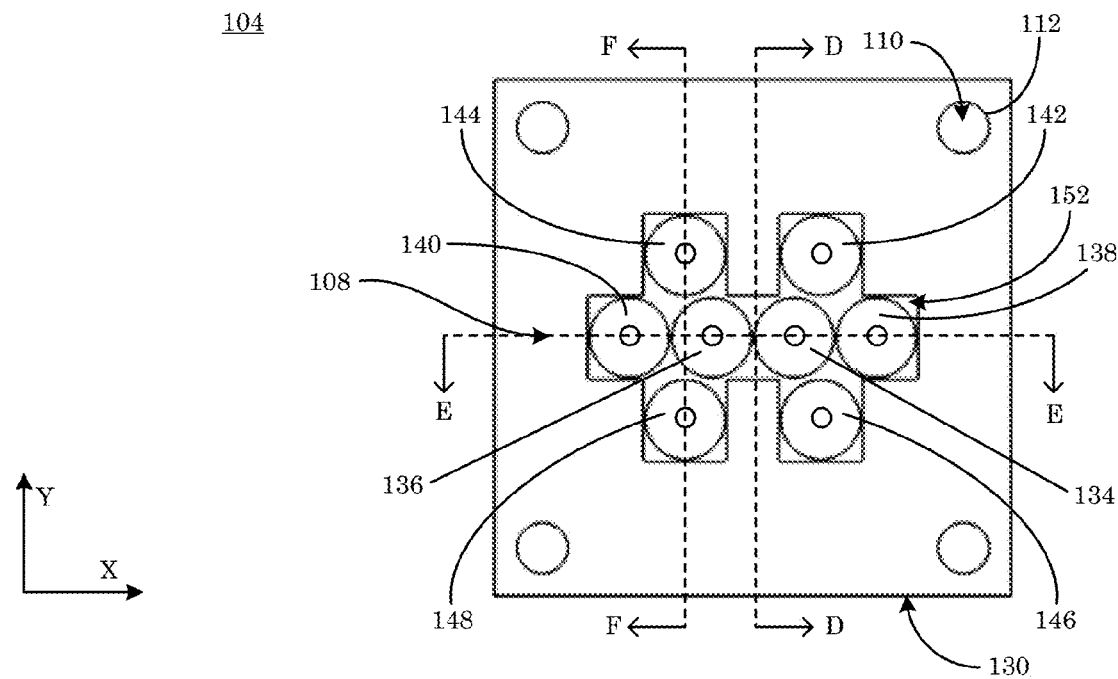
FIG. 22 shows a top view of the electrode chamber shown in FIG. 1.
Figure 23:
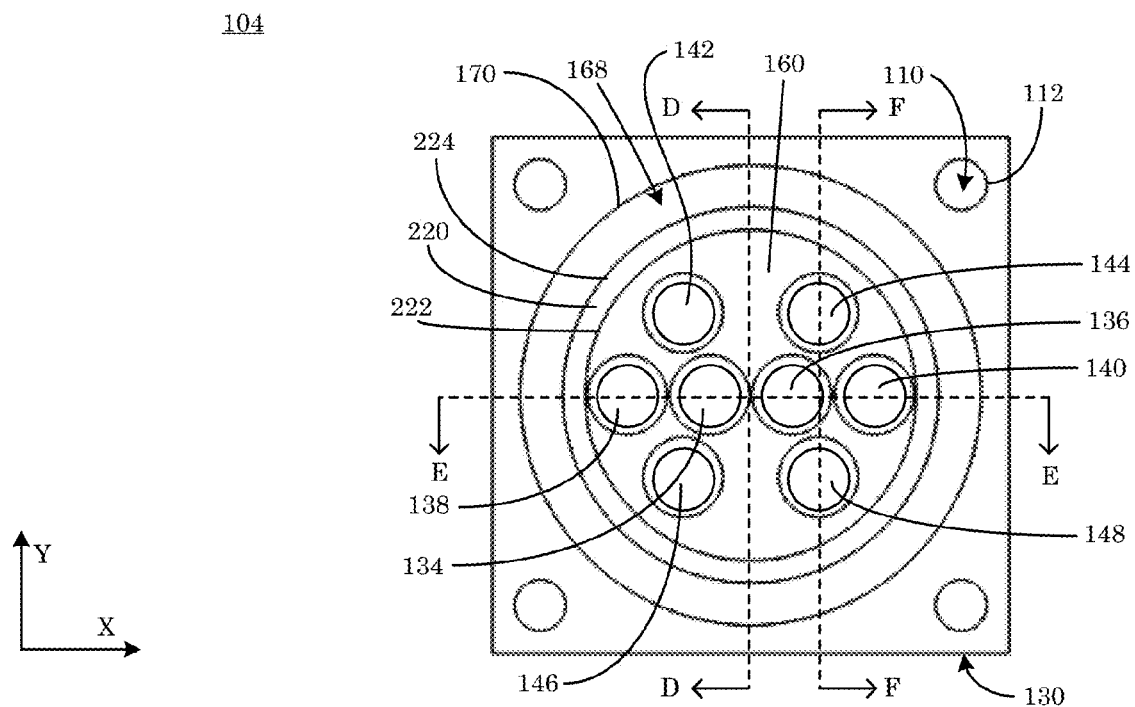
FIG. 23 shows a bottom view of the electrode chamber shown in FIG. 1.
Figure 24:
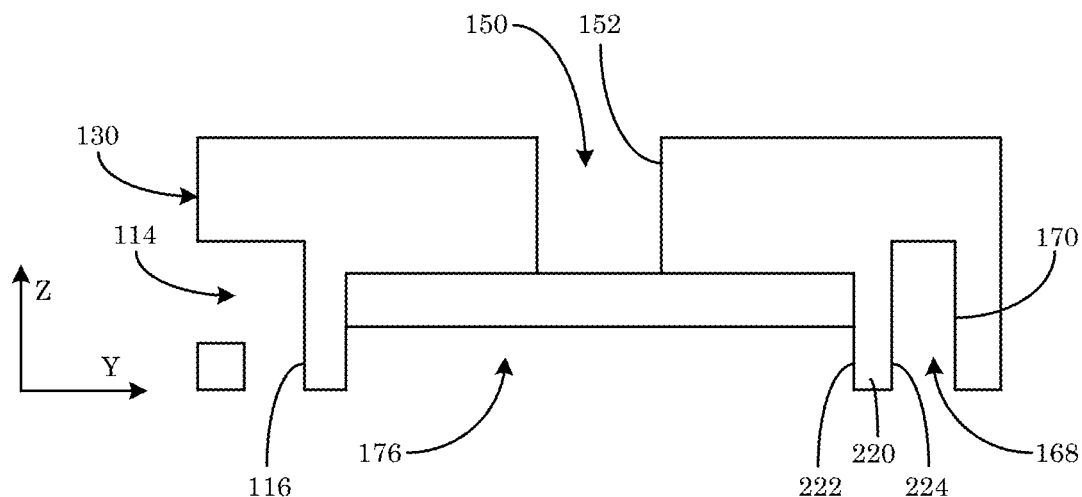
FIG. 24 shows a cross-section along line D-D of the electrode chamber shown in FIG. 22.
Figure 25:
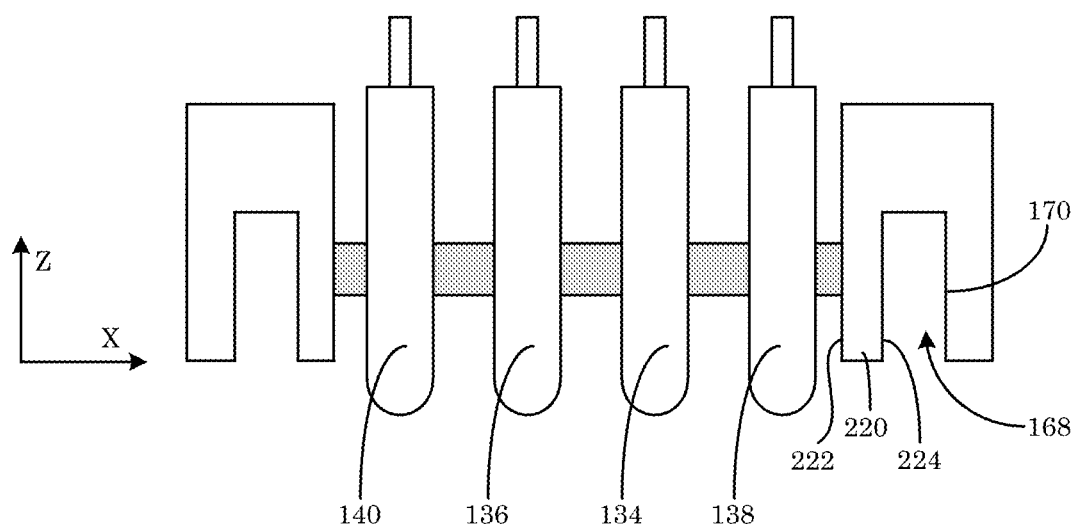
FIG. 25 shows a cross-section along line E-E of the electrode chamber shown in FIG. 22.
Figure 26:
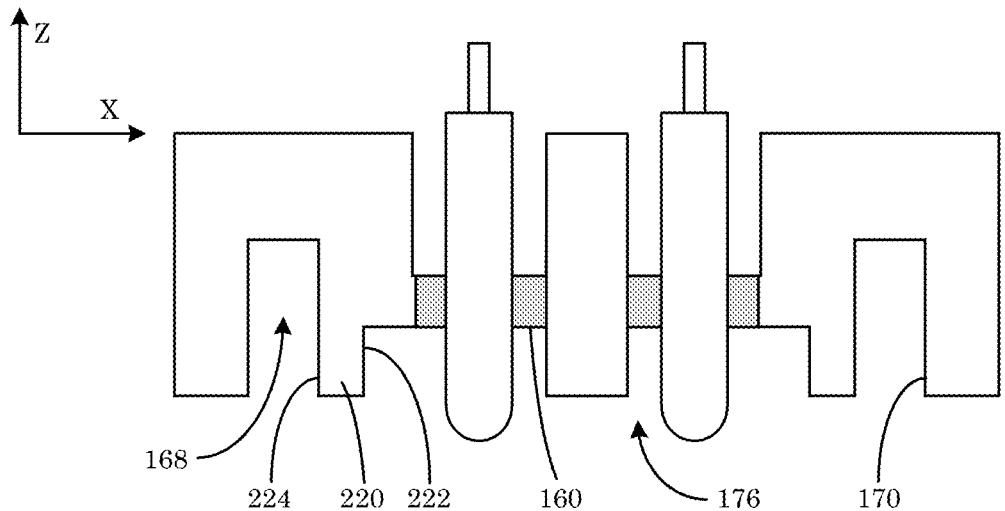
FIG. 26 shows a cross-section along line F-F of the electrode chamber shown in FIG. 22.
Figure 27:
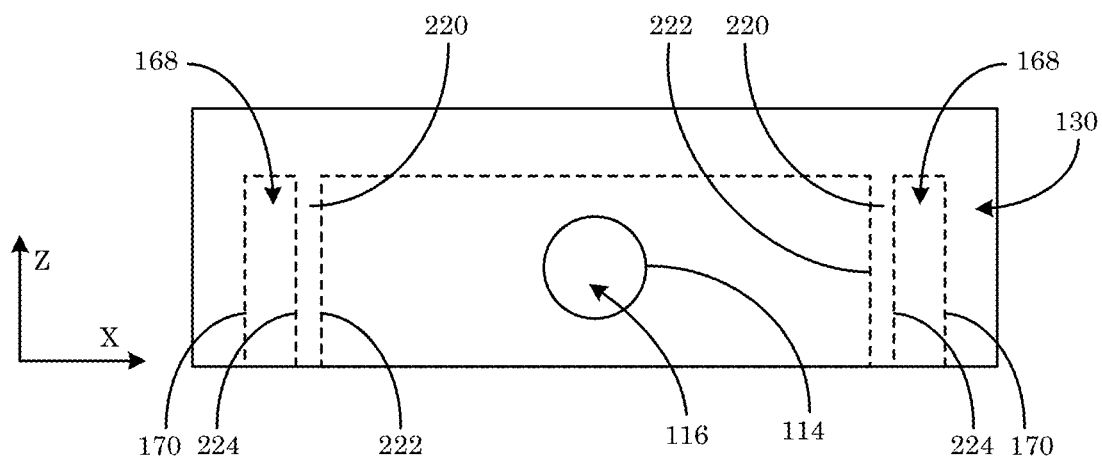
FIG. 27 shows an end view of the electrode chamber shown in FIG. 22.

According to an embodiment, susceptometer 100 includes electrode chamber 104 that, in combination with sample chamber 106, provides sample cavity 176 to receive sample 162, spool 164, and solenoid 166 disposed on spool 164. Here, electrode chamber 104 is shown in FIG. 18 (top perspective view of electrode chamber 104, not showing electrodes 108), FIG. 19 (bottom perspective view of electrode chamber 104, not showing electrodes 108), FIG. 20 (top perspective view of electrode chamber 104, showing electrodes 108), FIG. 21 (bottom perspective view of electrode chamber 104, showing electrodes 108), FIG. 22 (top view of electrode chamber 104), FIG. 23 (bottom view of electrode chamber 104), FIG. 24 (cross-section along line D-D shown in FIG. 22), FIG. 25 (cross-section along line E-E shown in FIG. 22), FIG. 26 (cross-section along line F-F shown in FIG. 22), FIG. 27 (end view of sample chamber 106). Aperture 110 bounded by wall 112 disposed in electrode chamber 104 receives a fastener and communicates the fastener to aperture 188 bounded by wall 190 in sample chamber 106 so that electrode chamber 104 is fastened to sample chamber 106. Although apertures 110 (electrode chamber 104) and apertures 188 (sample chamber 106) are shown in the figures for susceptometer 100, in a certain embodiment, electrode chamber 104 and sample chamber 106 that form chamber 102 can be monolithic (i.e., a single component) instead of separate components. In some embodiments, electrode chamber 104 and sample chamber 106 form chamber 102 by such as in a mold or extruder, or formed separately and adhered together (e.g., with an adhesive such as the epoxy), braised together, soldered together, clamped together, and the like.

Electrode chamber 104 includes electrode aperture 150 bounded by wall 152 such that electrodes 180 can protrude through electrode aperture 150 without contacting wall 152. In this manner, electrodes 180 are electrically isolated from wall 152 in electrode chamber 104. The shape of electrode aperture 150 can be any shape effective to provide protrusion of electrodes 180 through electrode aperture 150. Moreover, shape of electrode aperture 150 can be similar to a patterned arrangement of electrodes 180. In substrate 160. Substrate 160 is disposed in electrode chamber 104. Here, substrate 160 is received by and disposed inside inner wall 222 of protrusion 220 that also is bounded by outer wall 224. Outer wall 224 of protrusion 220 in combination with wall 170 forms solenoid receiver 168 that receives spool 164 on which solenoid 166 is disposed.

Electrode chamber 104 also includes aperture 116 bounded by wall 114 that traverses electrode chamber 104 from first end 130. Solenoid receiver 168 is in communication with aperture 116. In this manner, a wire can be disposed in and received by aperture 116 such that solenoid 166 disposed on spool 164 that is received by solenoid receiver 168 is connected to the wire when sample chamber 106 is contacted by electrode chamber 104. The wire can provide electrical communication to solenoid 166 even though solenoid 166 is not exposed beyond sample cavity 176 formed and enclosed by sample chamber 106 and electrode chamber 104.

According to an embodiment, susceptometer 100 includes electrodes 108 disposed in substrate 160 that is disposed in electrode chamber 104. Electrodes 108 are electrically conductive, engage and are in electrical contact with sample 162 when sample 162 is disposed in sample cavity 176 of chamber 102.

Figure 28:
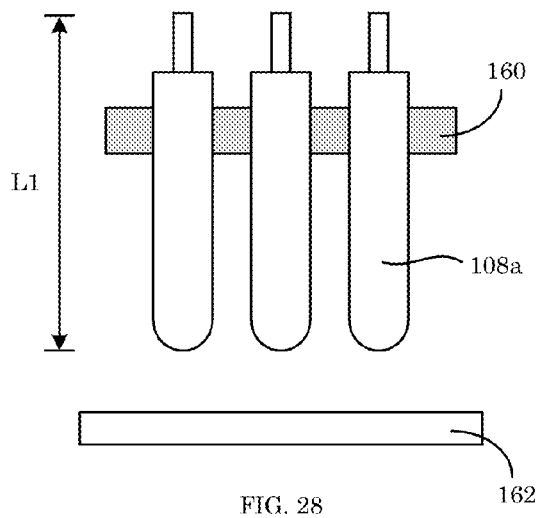
FIG. 28 shows a plurality of electrodes.
Figure 29:
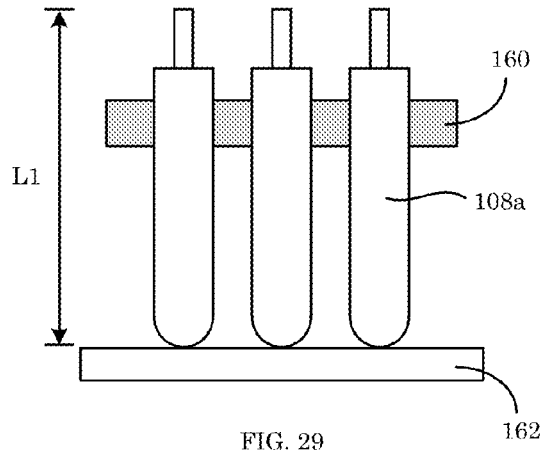
FIG. 29 shows the plurality of electrodes shown in FIG. 28 in contact with a sample.

In an embodiment, with reference to FIG. 28 and FIG. 29, electrodes 108 (here, electrodes 108*a*) are statically arranged in substrate 162 such that electrodes 108*a* have length L1 (FIG. 28) when not in contact with sample 162. In contact with sample 162, electrodes 108*a* and sample 162 experience a compressive force (FIG. 30) but electrodes 108*a* are adepressable by sample 162 such that electrodes 108*a* do not retract and maintain length L1. Electrodes 108*b* remain in electrical contact with sample 162 but do not experience a change in length from length L1. Exemplary electrodes 108 (e.g., 108*a*) that are adepressable include contact pins, probe pins, test probes, pin terminals, and the like.

Figure 30:
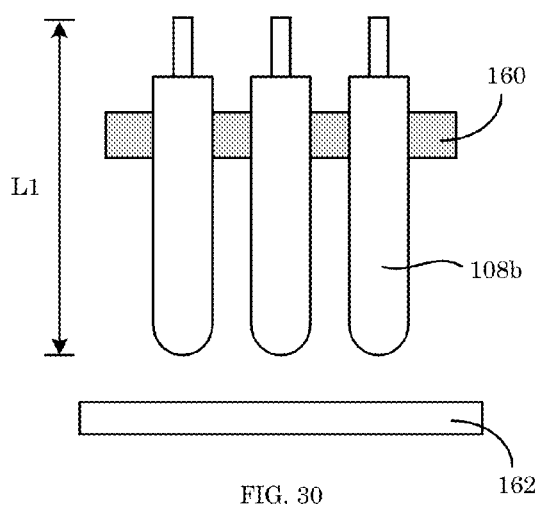
FIG. 30 shows a plurality of electrodes.
Figure 31:
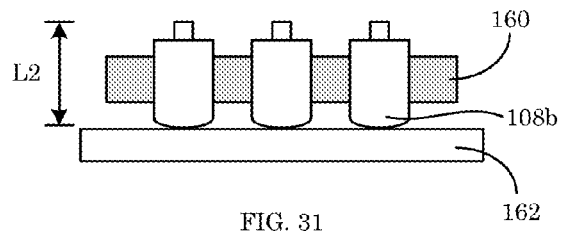
FIG. 31 shows the plurality of electrodes shown in FIG. 30 in contact with a sample.

In an embodiment, with reference to FIG. 30 and FIG. 31, electrodes 108 (here, electrodes 108*b*) are moveably depressable such that electrodes 108*b* have length L1 (FIG. 30) when not in contact with sample 162. In contact with sample 162, electrodes 108*b* and sample 162 experience a compressive force (FIG. 31) that causes electrodes 108*b* to retract from length L1 to length L2, which is shorter than length L1. During compression, electrodes 108*b* remain in electrical contact with sample 162. Exemplary electrodes 108 (e.g., 108*b*) that are movably depressible include spring-loaded contact pins, pogo pins, depressible contact pins, and the like.

Figure 32:
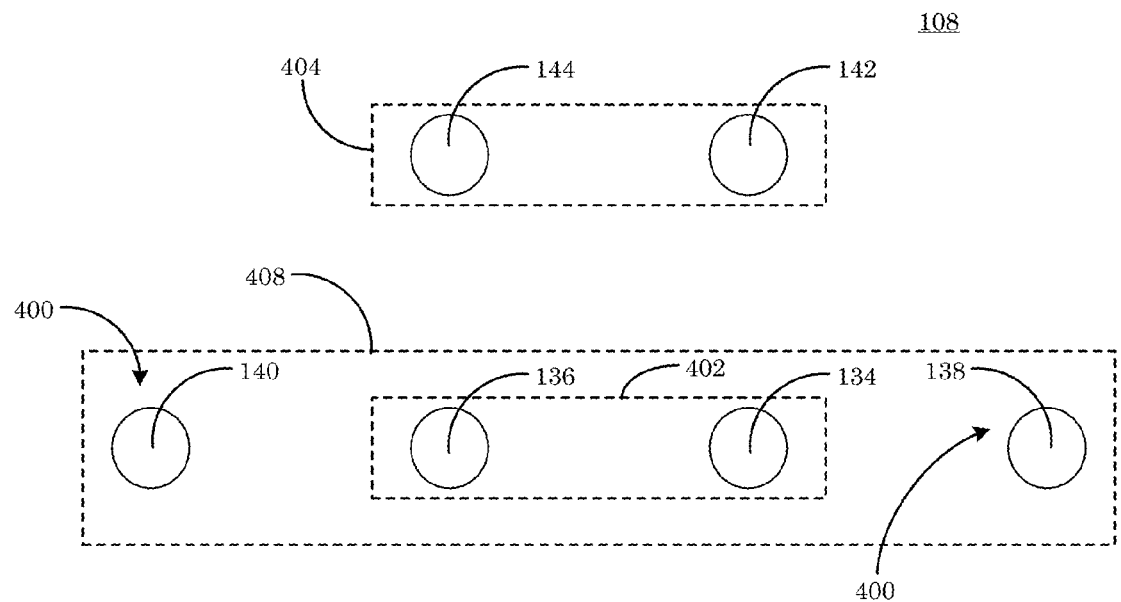
FIG. 32 shows a plurality of electrodes.
Figure 35:
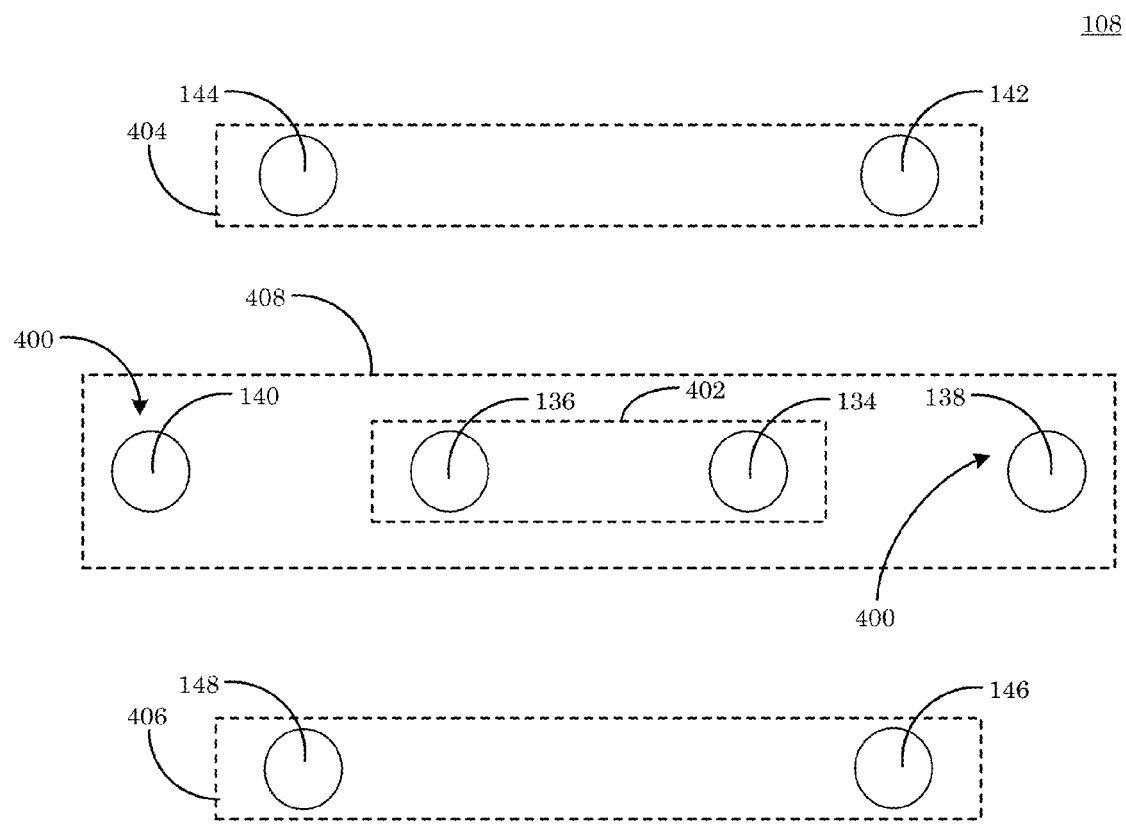
FIG. 35 shows a plurality of electrodes.

In an embodiment, as shown in FIG. 32 and FIG. 35, the plurality of electrodes 108 includes first pair 400 of electrodes (138, 140) disposed on substrate 160 and being electrically conductive to engage and be in electrical contact with sample 162; second pair 402 of electrodes (136, 134) disposed on substrate 160 and being electrically conductive to engage and be in electrical contact with sample 162, wherein second pair 402 of electrodes (136, 134) is arranged collinear with first pair 400 of electrodes (138, 140) to form a set 408 of aligned electrodes (400, 402 that includes electrodes 134, 136, 138, 140); and third pair 404 of electrodes (144, 142) disposed on substrate 160 and being electrically conductive to engage and be in electrical contact with sample 162, wherein third pair 404 of electrodes (144, 142) is arranged noncollinearly with set 408 of aligned electrodes. With reference to FIG. 35, electrodes 108 also can include fourth pair 406 of electrodes disposed (146, 148) on substrate 160 and being electrically conductive to engage and be in electrical contact with sample 162. Third pair 404 of electrodes (142, 144) are arranged parallel to set 408 of aligned electrodes (134, 136, 138, 140) (see FIG. 32 to FIG. 37).

A distance between adjacent electrodes 108 is not limited and can be any distance effective for susceptometer 100 to measure a Hall voltage of sample 162 or a current-in-plane resistance of 162. Further, electrodes 108 can be arranged in a variety of patterns in substrate 160. Whatever pattern electrodes 108 are arranged, electrodes 108 are arranged so that susceptometer 100 is configured to measure the Hall voltage of sample 162 or the current-in-plane resistance of 162. Furthermore, electrodes 108 (e.g., optionally disposed in chamber 102) are electrically reconfigurable in-situ and in contact with sample 162 to obtain reconfigurably the Hall voltage of sample 162 and the current-in-plane resistance of sample 162 and also subject sample 162 to a direct current (DC) electrical current. According to an embodiment, a switching member (not shown) is in electrical communication with electrodes 108 to reconfigure electrodes 108 between measuring the Hall voltage of sample 162 and the current-in-plane resistance of sample 162.

In an embodiment, as shown in FIG. 32 (and also FIG. 33 and FIG. 34), second pair 402 of electrodes (136, 134) and third pair 404 of electrodes are arranged in a square pattern such that electrode 134, electrode 136, electrode 142, and electrode 144 are each disposed in a corner of the square pattern. In an embodiment, as shown in FIG. 35 (and also FIG. 36 and FIG. 37), third pair 404 of electrodes (144, 142) and fourth pair 406 of electrodes (148, 146) are arranged in a square pattern such that electrode 142, electrode 144, electrode 146, and electrode 148 are each disposed in a corner of the square pattern. A spacing (e.g., pitch) among electrodes (134, 136, 138, 140) of set 408 of aligned electrodes is not limited and can be arbitrarily selected. Moreover, such spacing among electrodes (134, 136, 138, 140) of set 408 of aligned electrodes can be uniform (e.g., a uniform spacing) or non-uniform (e.g., a non-uniform spacing) between adjacent electrodes (134, 136, 138, 140) of set 408 of aligned electrodes.

Figure 33:
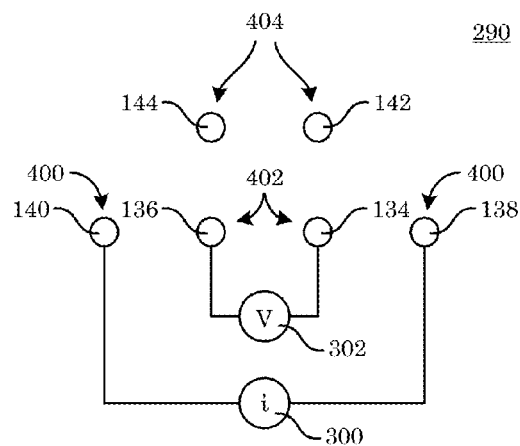
FIG. 33 shows the plurality of electrodes shown in FIG. 32 in a configuration to measure a current-in-plane resistance of a sample.

According to an embodiment, electrodes 108 are electrically reconfigurable in-situ and in contact with sample 162 to obtain reconfigurably the Hall voltage of sample 162 and the current-in-plane resistance of sample 162 and also subject sample 162 to a direct current (DC) electrical current. Here, electrodes 108 can be arranged as shown in FIG. 32 and configured electrically in resistance configuration 290 as shown in FIG. 33 to provide the current-in-plane resistance of sample 162, wherein first pair 400 of electrodes 138, 140 are in electrical communication with electrical current source 300, and second pair 402 of electrodes 134, 136 are in electrical communication with voltmeter 302. It is contemplated that electrical current source 300 provides electrical current that flows between electrode 140 and electrode 138 of first pair 400 in contact with sample 162. Moreover, voltmeter 302 determines a voltage difference across sample 162 via electrode 134 and electrode 136 of second pair 402.

Figure 34:
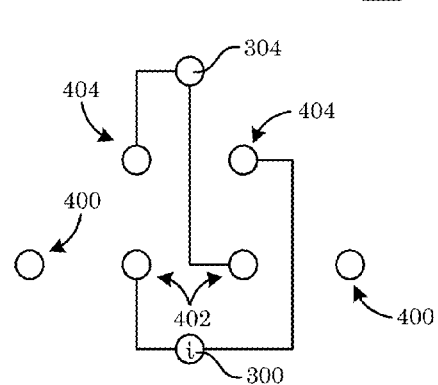
FIG. 34 shows the plurality of electrodes shown in FIG. 32 in a configuration to measure a Hall voltage of a sample.

In an embodiment, electrodes 108 are arranged as shown in FIG. 32 and configured electrically in Hall voltage configuration 292 as shown in FIG. 34 to provide the Hall voltage of sample 162, wherein electrodes 136, 142 are in electrical communication with electrical current source 300, and electrodes 134, 144 are in electrical communication with phase sensitive detector 304. It is contemplated that electrical current source 300 provides electrical current that flows between electrode 136 and electrode 142 in contact with sample 162. Moreover, phase sensitive detector 304 determines a voltage difference across sample 162 via electrode 134 and electrode 144.

According to an embodiment, electrodes 108 are electrically reconfigurable in-situ and in contact with sample 162 between resistance configuration 290 shown in FIG. 33 and Hall voltage configuration 292 shown in FIG. 34 to obtain reconfigurably the Hall voltage of sample 162 (per Hall voltage configuration 292) and the current-in-plane resistance of sample 162 (per resistance configuration 290) while subjecting sample 162 to DC electrical current from electrical current source 300.

Figure 36:
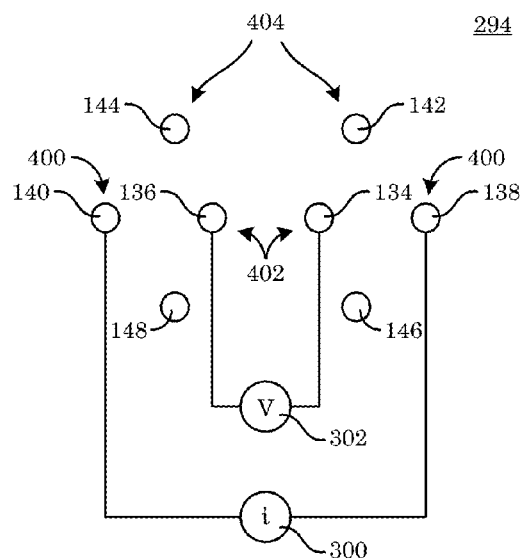
FIG. 36 shows the plurality of electrodes shown in FIG. 35 in a configuration to measure a current-in-plane resistance of a sample.

In an embodiment, electrodes 108 are arranged as shown in FIG. 35 and configured electrically in resistance configuration 294 as shown in FIG. 36 to provide the current-in-plane resistance of sample 162, wherein first pair 400 of electrodes 138, 140 are in electrical communication with electrical current source 300, and second pair 402 of electrodes 134, 136 are in electrical communication with voltmeter 302. It is contemplated that electrical current source 300 provides electrical current that flows between electrode 140 and electrode 138 of first pair 400 in contact with sample 162. Moreover, voltmeter 302 determines a voltage difference across sample 162 via electrode 134 and electrode 136 of second pair 402.

Figure 37:
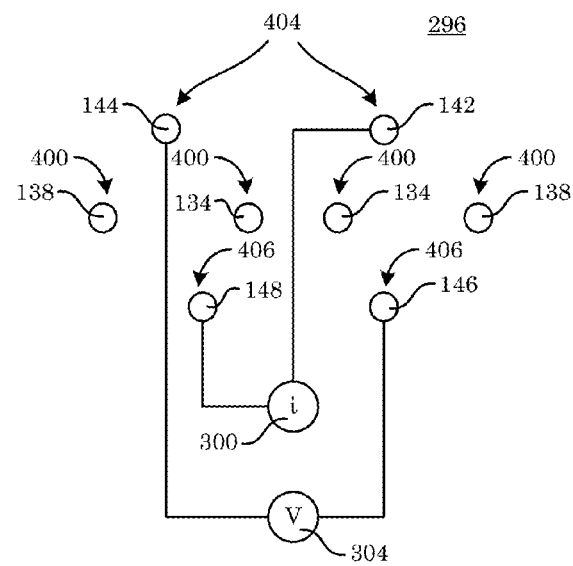
FIG. 37 shows the plurality of electrodes shown in FIG. 35 in a configuration to measure a Hall voltage of a sample.

In an embodiment, electrodes 108 are arranged as shown in FIG. 35 and configured electrically in Hall voltage configuration 296 as shown in FIG. 37 to provide the Hall voltage of sample 162, wherein electrodes 148, 142 are in electrical communication with electrical current source 300, and electrodes 146, 144 are in electrical communication with phase sensitive detector 304. It is contemplated that electrical current source 300 provides electrical current that flows between electrode 148 and electrode 142 in contact with sample 162. Moreover, phase sensitive detector 304 determines a voltage difference across sample 162 via electrode 146 and electrode 144.

According to an embodiment, electrodes 108 are electrically reconfigurable in-situ and in contact with sample 162 between resistance configuration 294 shown in FIG. 36 and Hall voltage configuration 296 shown in FIG. 37 to obtain reconfigurably the Hall voltage of sample 162 (per Hall voltage configuration 296) and the current-in-plane resistance of sample 162 (per resistance configuration 294) while subjecting sample 162 to DC electrical current from electrical current source 300.

Although FIG. 32 to FIG. 37 show a certain number of electrodes 108, any number electrodes effective to be electrically reconfigurable in-situ and in contact with sample 162 to provide reconfigurably the Hall voltage of sample 162 and the current-in-plane resistance of sample 162 (while subjecting sample 162 to the DC electrical current) can be used. In an embodiment, half of a total number of electrodes 108 are current lines and half of the total number of electrodes 108 are voltage lines.

Figure 38:
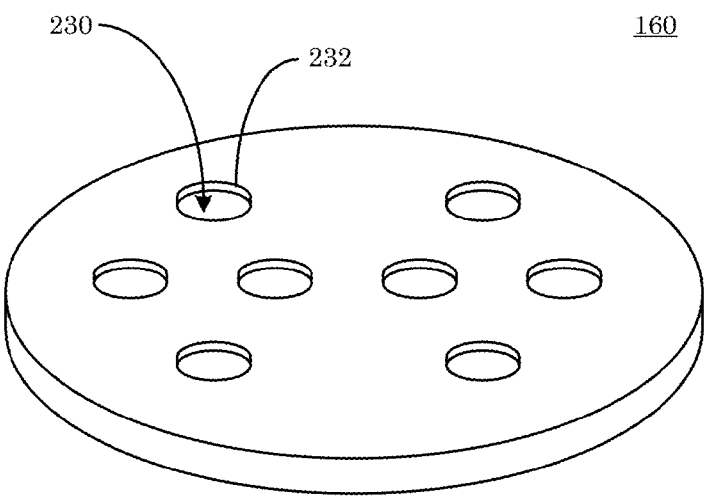
FIG. 38 shows a perspective view of a substrate.
Figure 39:
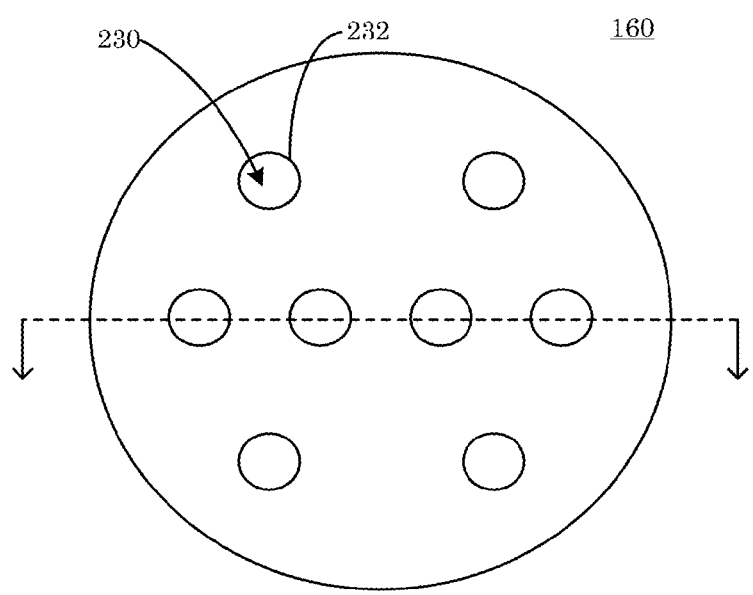
FIG. 39 shows a top view of the substrate shown in FIG. 38.
Figure 40:
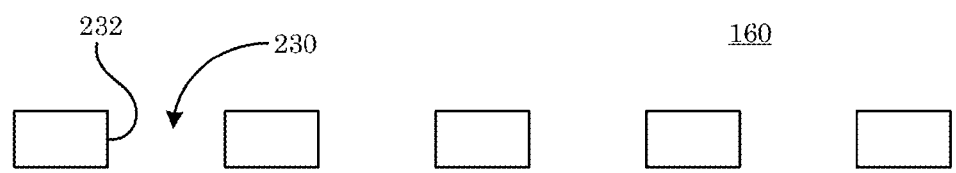
FIG. 40 shows a side view of the substrate shown in FIG. 38.
Figure 41:
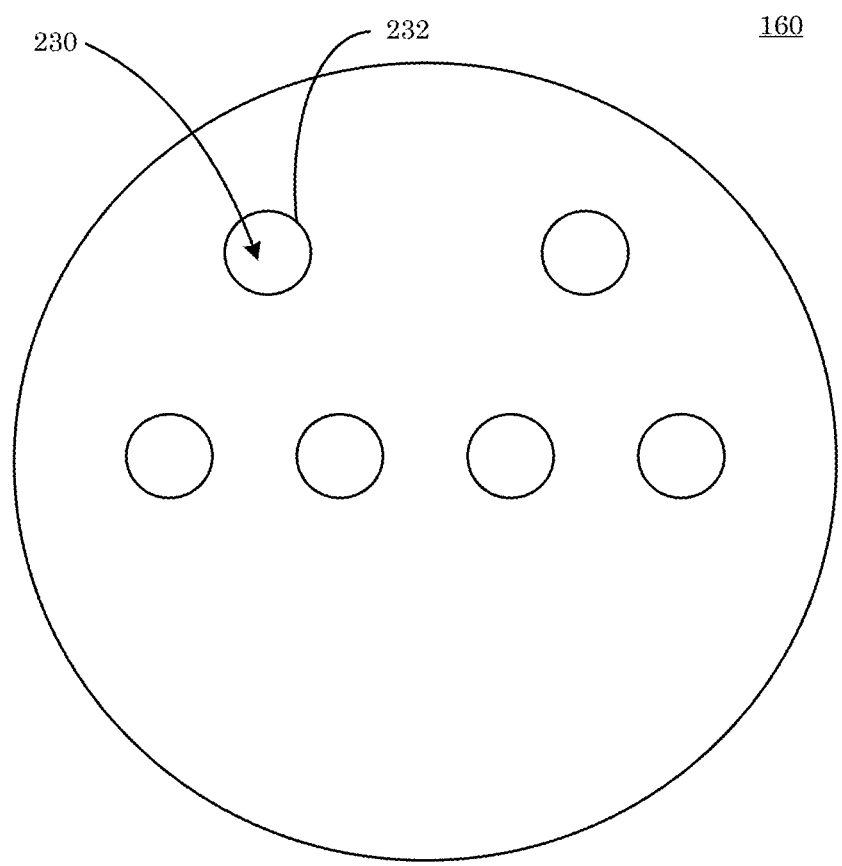
FIG. 41 shows a perspective view of a substrate.

According to an embodiment, susceptometer 100 includes substrate 160 that is disposed in electrode chamber 104 and in which electrodes 108 are disposed. With reference to FIG. 38 (perspective view of substrate 160), FIG. 39 (top view of substrate 160), and FIG. 40 (cross-section along line G-G shown in FIG. 39), substrate 160 includes a plurality of apertures 230 bounded by wall 232 that receive, electrodes 180. Substrate 160 is received by protrusion 220 of the electrode chamber 104 and is engaged by inner wall 222 of protrusion 220. Substrate 160 electrically isolates electrodes 108 from each other and also electrically isolates electrodes 108 from wall 152 and inner wall electrode chamber 104. Substrate 160 can be attached by a fastener or bonded to electrode chamber 104. In an embodiment, substrate 160 can be removably disposed in electrode chamber 104 so that substrate 160 can be removed from electrode chamber 104 while maintaining electrodes 108 in substrate 160. In this manner, a different plurality of electrodes 108 can be disposed in electrode chamber 104 by removing and substituting different substrates 160 that include different electrodes 108. The number of apertures 230 in substrate 160 can be selected, e.g., based on a number of electrodes as shown in FIG. 39 and FIG. 41 (top view of an embodiment of substrate 160 that includes six apertures 230 arranged to receive electrodes 108 as shown in FIG. 32).

Figure 42:
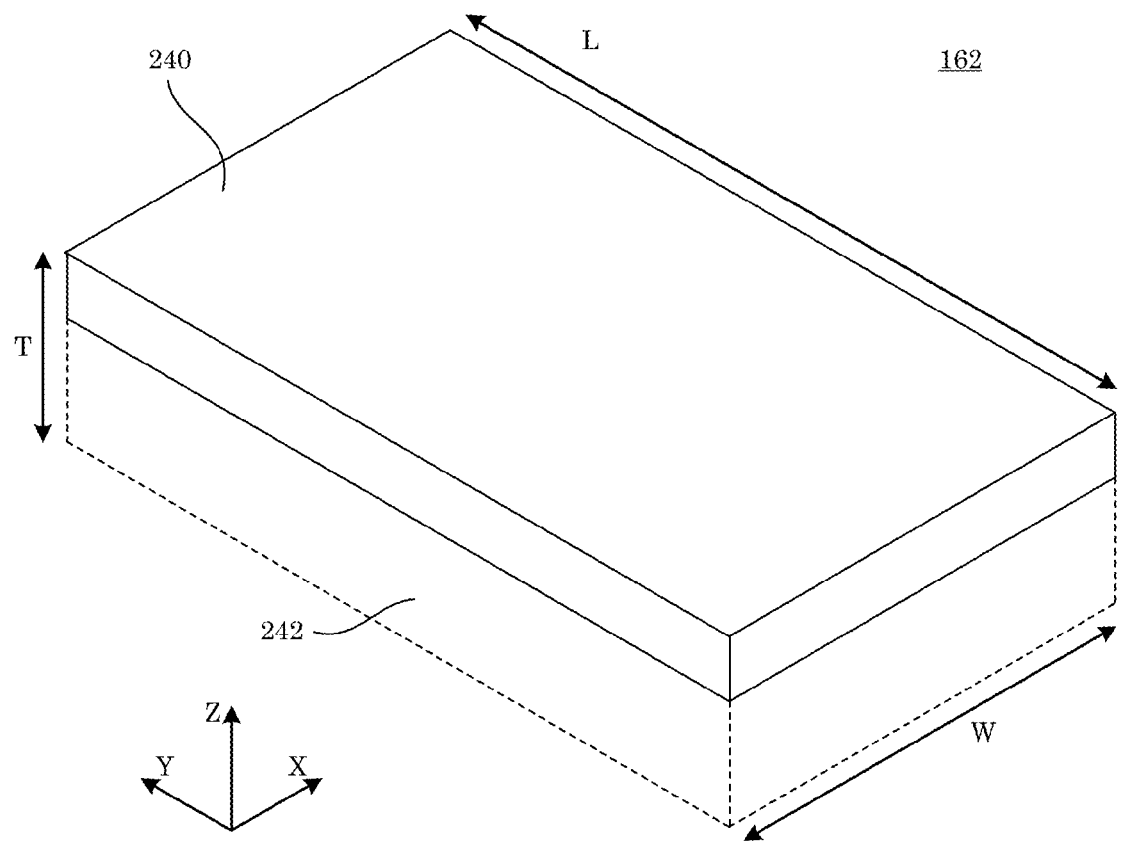
FIG. 42 shows a sample.

In an embodiment, susceptometer 100 receives sample 162 in sample cavity 176 within chamber 102 formed by electrode chamber 104 and sample chamber 106. Susceptometer 100 subjects sample 162 to a primary magnetic field produced by solenoid 166 and DC electric current from electrodes 108 to perform magnetic susceptometry. As shown in FIG. 42, sample 162 can include analyte layer 240 and optional base layer 242, wherein analyte layer 240 is disposed on the optional base layer 242. Electrodes 108 make electrical contact with analyte layer 240 that is subjected to magnetic susceptometry in susceptometer 100. In some embodiments, sample 162 includes analyte layer 240. According to an embodiment, sample 162 is a laminate structure that includes analyte layer 240 disposed on base layer 242. In a certain embodiment, sample 162 can include a plurality of layers that includes a plurality of analyte layers 240, wherein individual analyte layers 240 are a same composition or different composition.

In some embodiments, sample 162 includes a thin film, e.g., analyte layer 240 can be a thin film. In a certain embodiment, sample 162 includes a semiconductor thin film, a ferromagnetic thin film, or a combination thereof. Exemplary semiconductor thin films include gallium arsenide, indium gallium arsenide or indium arsenide, and the like. exemplary ferromagnetic thin films include cobalt-iron-boron, cobalt-platinum, iron-palladium alloys and the like. exemplary base layers 242 include aluminum oxide (alumina), silicon, glass (silica), titanium dioxide and the like.

Sample 162 can have a length L from 0.5 millimeters (mm) to 150 mm, specifically from 1 millimeters (mm) to 25 mm, and more specifically from 5 millimeters (mm) to 10 mm. Sample 162 can have a width W from 0.5 millimeters (mm) to 150 mm, specifically from 1 millimeters (mm) to 25 mm, and more specifically from 5 millimeters (mm) to 10 mm. Sample 162 can have a thickness T from 0.1 millimeters (mm) to 10 mm, specifically from 0.2 millimeters (mm) to 2 mm, and more specifically from 0.3 millimeters (mm) to 0.75 mm.

According to an embodiment, susceptometer 100 includes solenoid 166 that is disposed on spool 164. Spool 164 includes winding member 420 on which solenoid 166 is disposed, platen 422 disposed on inner wall 426 of winding member 420 that bounds and is an inner diameter of central space 424. Platen 420 includes aperture 185 bounded by wall 187, wherein aperture 185 receives a fastener to fasten spool 164 two platform 180 of sample chamber 106. Platen 420 receives sample platform 178 that is fastened to platen 420 and sample chamber 106 via apertures 185 of spool 164. Spool 164 also includes flanges 428, 430 disposed at opposing ends of winding member 420. Flange 428 is received by solenoid receiver 168 of electrode chamber 104. Flange 430 is received by solenoid receiver 172 of sample chamber 106.

Solenoid 166 is windingly disposed around winding member 420 of spool 164 in a helical shape. Solenoid 166 includes a plurality of windings 450 that traverses a length of solenoid 166 and terminate in first end 456 and second end 458 disposed at opposing ends of solenoid 166. The plurality of windings 450 form an inner wall 454 that bounds solenoid cavity 452. Solenoid cavity 452 receives electrodes 188 disposed proximate to first end 456, sample 162, sample platform 178, and platform 180. Solenoid 166 receives electrical current, e.g., from electrical current source 300, that flows between first end 456 and second end 458. Solenoid 166 can be, e.g., a wound wire that includes electrically insulation surrounding the wire to insulate the plurality of windings 450 from each other and spool 164, as well as chamber 102. The number of windings 450 present in solenoid 166 can be selected to produce a primary magnetic field in response to the electrical current subjected to solenoid 166 as current flows between first end 456 and second end 458. First end 456 and second end 458 are in electrical communication with electrical wiring to receive the electrical current, e.g., from electrical current source 300.

In an embodiment, susceptometer 100 includes substrate 160; the plurality of electrodes 108 to subject sample 162 to the direct current electrical current and to measure the Hall voltage of sample 162 or the current-in-plane resistance of sample 162, the plurality of electrodes 108 including: first pair 400 of electrodes (140, 138) disposed on substrate 160 and being electrically conductive to engage and be in electrical contact with sample 162; second pair 402 of electrodes (136, 134) disposed on substrate 160 and being electrically conductive to engage and be in electrical contact with sample 162, second pair 402 of electrodes (136, 134) arranged collinear with first pair 400 of electrodes (140, 138) to form set 408 of aligned electrodes (134, 136, 138, 140); and third pair 404 of electrodes (144, 142) disposed on substrate 160 and being electrically conductive to engage and be in electrical contact with sample 162, third pair 404 of electrodes arranged noncollinearly with set 408 of aligned electrodes (134, 136, 138, 140); and solenoid 166 circumscribingly disposed around electrodes 188 to: receive sample 162 such that solenoid 166 is circumscribingly disposed around sample 162; receive an alternating current and produce a primary magnetic field based on the alternating current; and subject sample 162 to the primary magnetic field.

According to an embodiment, susceptometer 100 further includes a magnet disposed proximate to electrodes 108 and solenoid 166 to provide a secondary magnetic field to sample 162, wherein the magnet is disposed external to solenoid 166.

According to an embodiment, susceptometer 100 further includes a heater to heat sample 162, the heater disposed proximate to sample 162.

According to an embodiment, susceptometer 100 further includes a switching member to switch pairs (e.g., 400, 402, 404, 406) of electrodes 108 between resistance configuration (e.g., 290, 294) and Hall voltage configuration (e.g., 292, 296), wherein the switching member is in electrical communication with the plurality of electrodes 108.

According to an embodiment, susceptometer 100 further includes phase sensitive detector 304 to detect a voltage response of sample 162 that is produced in response to the primary magnetic field, wherein the voltage response occurs at a primary frequency of the primary magnetic field.

According to an embodiment, susceptometer 100 further includes chamber 102 in which substrate 162, electrodes 108, and solenoid 166 are disposed.

According to an embodiment, electrodes 108 are moveably depressable such that electrodes 108 retract and remain in electrical contact with sample 162.

According to an embodiment, electrodes 108 are statically arranged in substrate 160 to be adepressable by sample 162 and provide electrical contact with sample 162.

According to an embodiment, third pair 404 of electrodes are arranged parallel to set 408 of aligned electrodes, and second pair 402 of electrodes and third pair 404 of electrodes are arranged to obtain the Hall voltage of sample 162.

According to an embodiment, the plurality of electrodes 108 further includes fourth pair 406 of electrodes (146, 148) disposed on substrate 160 and being electrically conductive to engage and be in electrical contact with sample 162, wherein third pair 404 of electrodes and fourth pair 406 of electrodes are arranged to obtain the Hall voltage from sample 162.

According to an embodiment, half of the total number of electrodes 108 are current lines, and half of the total number of electrodes 108 are voltage lines.

According to an embodiment, electrodes 108 are electrically reconfigurable in-situ and in contact with sample 162 to obtain reconfigurably the Hall voltage of sample 162 and the current-in-plane resistance of sample 162.

According to an embodiment, substrate 160 electrically isolates the plurality of electrodes 108 from each other.

According to an embodiment, susceptometer 100 further includes sample 162, wherein sample 162 includes a thin film.

According to an embodiment, susceptometer 100 further includes sample 162, wherein sample 162 includes a semiconductor thin film, a ferromagnetic thin film, or a combination thereof.

According to an embodiment, the primary magnetic field includes a magnetic field direction that varies in response to the alternating current and is perpendicular to a surface of sample 162 that is in contact with electrodes 108.

In an embodiment, susceptometer 100 is configured to perform magnetic susceptometry on sample 162 and includes: chamber 102; substrate 160 disposed in chamber 102; the plurality of electrodes 108 disposed in chamber 102 and being electrically reconfigurable in-situ and in contact with sample 162 to obtain reconfigurably the Hall voltage of sample 162 and the current-in-plane resistance of sample 162 and to subject sample 162 to a direct current electrical current, the plurality of electrodes 108 includes: first pair 400 of electrodes disposed on substrate 160 and being electrically conductive to engage and be in electrical contact with sample 162; second pair 402 of electrodes disposed on substrate 160 and being electrically conductive to engage and be in electrical contact with sample 162, second pair 402 of electrodes arranged collinear with first pair 400 of electrodes to form set 408 of aligned electrodes; and third pair 404 of electrodes disposed on substrate 160 and being electrically conductive to engage and be in electrical contact with sample 162, third pair 404 of electrodes arranged noncollinearly with set 408 of aligned electrodes; and fourth pair 406 of electrodes disposed on substrate 160 and being electrically conductive to engage and be in electrical contact with sample 162, fourth pair 406 of electrodes arranged noncollinearly with set 408 of aligned electrodes and arranged in a square pattern with third pair 404 of electrodes; and solenoid 166 disposed in chamber 102 and circumscribingly disposed around electrodes 108 to: receive sample 162 such that solenoid 166 is circumscribingly disposed around sample 162; receive an alternating current and produce a primary magnetic field based on the alternating current; and subject sample 162 to the primary magnetic field.

A size of chamber 102 can be any size effective to receive sample 162 and to subject sample 162 to magnetic susceptometry. Chamber 102 of susceptometer 102 can have a width, length, and thickness respectively along axes X, Y, and Z as shown in FIG. 1. The width can be, e.g., from 500 micrometers (μm) to 1.0 centimeters (cm), specifically from 2 millimeters (mm) to 5 cm, and more specifically from 8 mm to 2 cm. The length can be, e.g., from 500 micrometers (μm) to 20 centimeters (cm), specifically from 2 millimeters (mm) to 10 cm, and more specifically from 8 mm to 4 cm. The thickness can be, e.g., from 500 micrometers (μm) to 5 centimeters (cm), specifically from 2 millimeters (mm) to 3 cm, and more specifically from 8 mm to 2 cm.

Figure 43:
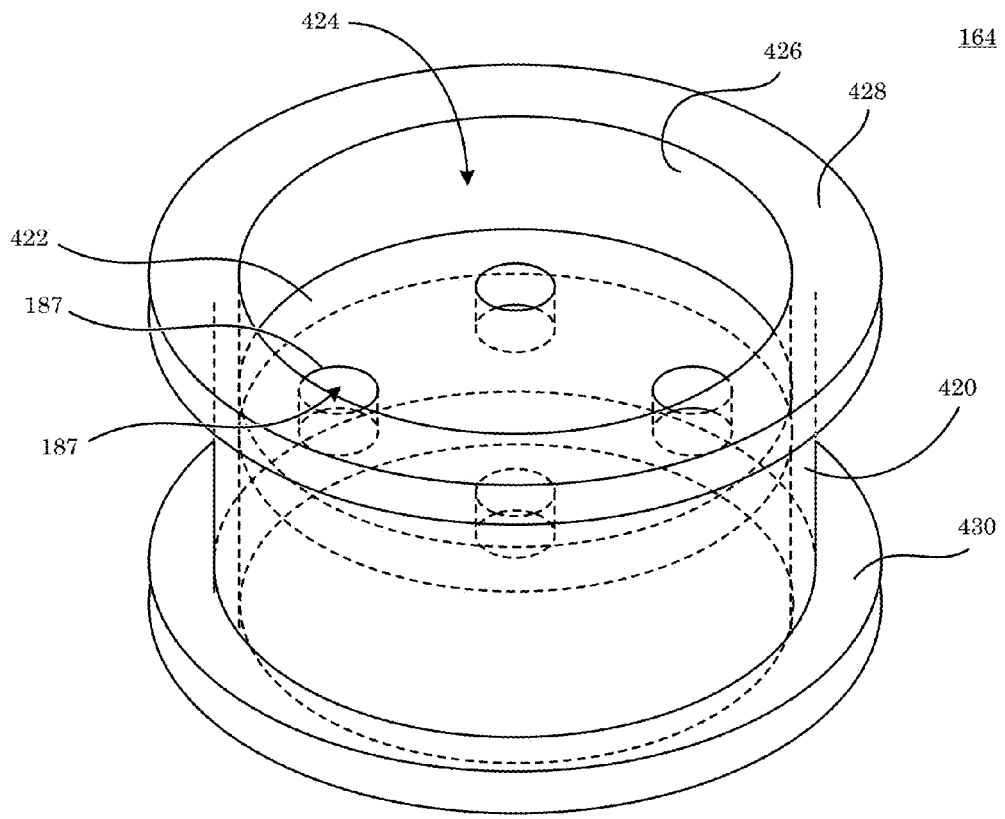
FIG. 43 shows a perspective view of the spool.
Figure 44:
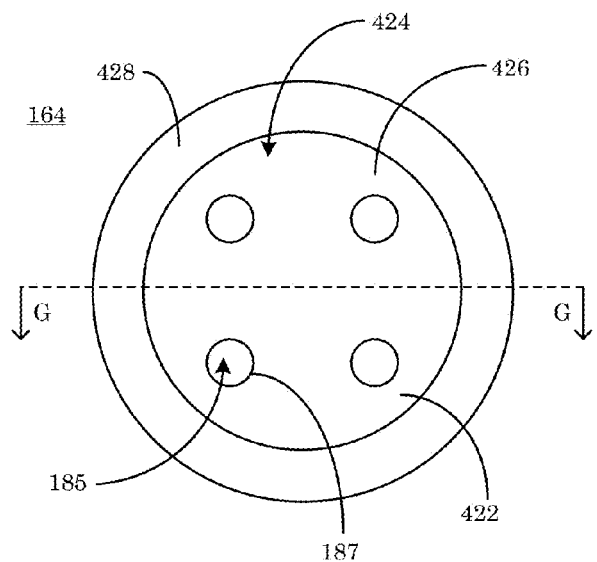
FIG. 44 shows a top view of the spool shown in FIG. 33.
Figure 45:
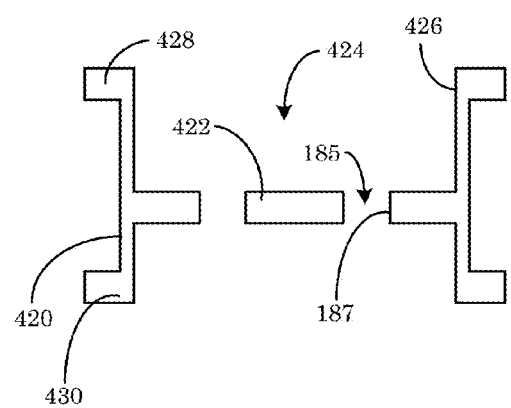
FIG. 45 shows a cross-section along line G-G shown in FIG. 44.
Figure 46:
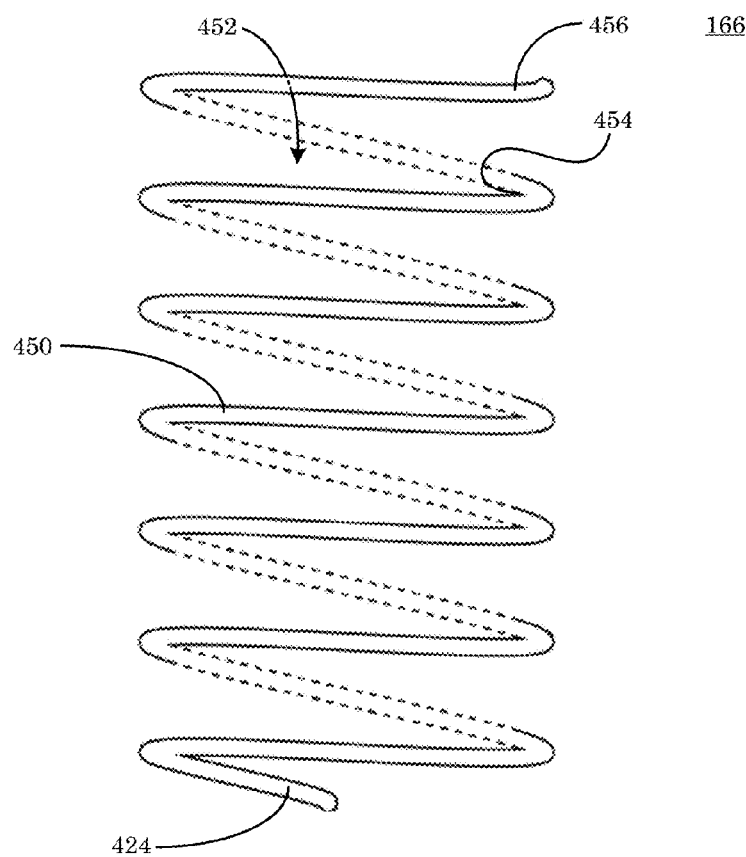
FIG. 46 shows a perspective view of a solenoid.
Figure 47:
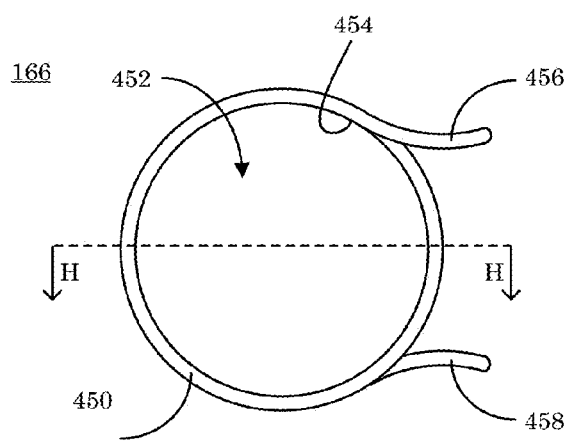
FIG. 47 shows a top view of the solenoid shown in FIG. 46.
Figure 48:
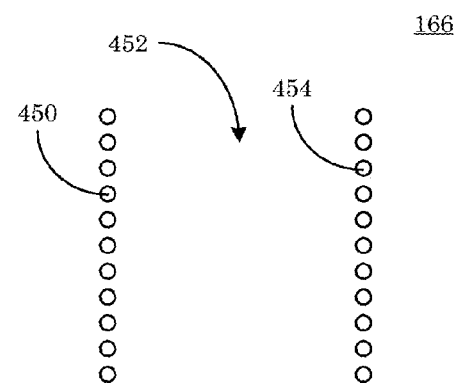
FIG. 48 shows a cross-section along line H-H shown in FIG. 47.

A size of spool 164 can be any size effective to receive sample 162 and also receive, solenoid 166 and subject sample 162 to magnetic susceptometry. Spool 164 of susceptometer 102 can have a primary diameter and primary thickness, as shown in FIG. 43 and have a top/bottom lip diameter and top/bottom lip thickness, as shown in FIG. 43. The primary diameter can be from 500 micrometers (μm) to 1.0 centimeters (cm), specifically from 2 millimeters (mm) to 10 cm, and more specifically from 8 mm to 4 cm. The primary thickness can be from 500 micrometers (μm) to 10 centimeters (cm), specifically from 2 millimeters (mm) to 10 cm, and more specifically from 8 mm to 2 cm.

A size of Solenoid 166 can be any size effective to circumscribe spool 164 and to receive sample 162 and to subject sample 162 to magnetic susceptometry. Solenoid 162 is composed of a single wire loop and can have a loop diameter, wire diameter and a number of wire turns. The loop diameter can be from 500 micrometers (μm) to 10 centimeters (cm), specifically from 2 millimeters (mm) to 10 cm, and more specifically from 8 mm to 4 cm. The wire diameter can be from 80 micrometers (μm) to 1 millimeter (mm), specifically from 100 micrometers (μm) to 800 micrometers (μm), more specifically form 250 micrometers (μm) to 500 micrometers (μm), The number of wire turns can be from 1 turn to 100 turns, specifically from 10 turns to 50 turns, more specifically from 20 turns to 30 turns.

Substrate 160 can be electrically insulating or electrically conductive. Exemplary materials for substrate 160 include Polyether ether ketone (PEEK) plastic, alumina, acrylic, teflon, brass, copper, aluminum and the like.

Sample 162 can be electrically insulating or electrically conductive. The surfaces of sample 162 may be both electrically insulating and electrically conductive. Specifically, a bottom surface that is touching Sample platform 178 may be electrically insulating, while a top surface that is touching the plurality of electrodes 108 may be electrically conductive. Exemplary materials for sample 162 can be silicon, glass, cobalt-iron-boron alloy, iron-palladium alloy, and cobalt-platinum multilayers.

Sample platform 178 can be electrically insulating or electrically conductive. Sample platform 178 can also be thermally insulating or thermally conductive. Exemplary materials for sample platform 178 can be brass, copper, glass, alumina, polyether ether ketone (peek) plastic, teflon, aluminum and the like.

Spool 164 can be electrically insulating or electrically conductive. Sample platform 178 can also be thermally insulating or thermally conductive. exemplary materials for spool 164 can be brass, copper, glass, alumina, polyether ether ketone (PEEK) plastic, teflon, aluminum and the like.

Solenoid 166 can be thermally conductive or thermally insulating. Solenoid 166 must be electrically conductive, but may contain electrical insulation on some or all of its exterior surfaces. Exemplary samples can be copper, brass, nickel, aluminum, gold, platinum, silver, tungsten and the like.

Electrodes 108 can be can be thermally conductive or thermally insulating. Electrodes 108 must be electrically conductive, but may contain electrical insulation on some or all of its exterior surfaces. Exemplary samples can be copper, brass, nickel, aluminum, gold, platinum, silver, tungsten and the like.

Electrode chamber 104 can be electrically insulating or electrically conductive. Electrode chamber 104 can also be thermally insulating or thermally conductive. exemplary samples can be brass, copper, glass, alumina, polyether ether ketone (PEEK) plastic, Teflon, aluminum and the like.

Sample chamber 106 can be electrically insulating or electrically conductive. Sample chamber 106 can also be thermally insulating or thermally conductive. Exemplary samples can be brass, copper, glass, alumina, polyether ether ketone (PEEK) plastic, Teflon, aluminum and the like.

Mount 200 that includes couplers 202, 204, 206 can be electrically insulating or electrically conductive. Mount 200 can also be thermally insulating or thermally conductive. Exemplary samples can be brass, copper, glass, alumina, polyether ether ketone (PEEK) plastic, teflon, aluminum and the like.

In an embodiment, with reference to FIG. 6, a process for making susceptometer 100 includes mechanically etching raw material into two rectangular solids whose lengths, widths and heights match that of electrode chamber 104 and sample chamber 106. The process also includes mechanically etching apertures into the two solid rectangular prisms in the various locations identified in FIG. 6, matching the design drawing of electrode chamber 104 and sample chamber 106. A process for making susceptometer 100 also includes mechanically etching material into a rectangular solid with four apertures etched symmetrically around the edges, matching the design drawing identified in FIG. 6, of sample platform 178. A process for making susceptometer 100 also includes mechanically etching material into the shape of a spool with a platform along the spool centerline as identified in FIG. 6, matching the design drawing of spool 164. According to an embodiment, a process for making susceptometer 100 includes mechanically etching Mount 200 into a shape that mates with the aperture 150 and with apertures to mate with electrodes 108. In an embodiment, with reference to FIG. 6, a process for making susceptometer 100 includes mating Mount 200 with aperture 150 using an adhesive epoxy glue. According to an embodiment, a process for making susceptometer 100 includes mating electrodes 108 with mount 200 using an adhesive epoxy glue. According to an embodiment, a process for making solenoid 166 includes creating a plurality of windings 450 with an equal number of windings per length and a winding radius determined by the size of the inscribed spool 164. According to an embodiment, a process for making solenoid 166 includes a semi-permanent mounting to spool 164 using an adhesive epoxy glue. According to an embodiment, a process for making solenoid 166 includes the wire ends 456 and 458 releasing from spool 164 and terminating a distance away from spool 164 in the direction of aperture 118 of sample chamber 106. According to an embodiment, a process for making susceptometer 100 includes placing a sample 162 onto mount 200, and placing mount 200 into spool 164 and placing spool 164 into sample chamber 106 and placing electrode chamber 104 on top of sample chamber 106 and using a plurality of screws through the apertures referenced in FIG. 6 to secure the entire assembly together.

Susceptometer 100 advantageously can have a selected measurement operation bandwidth. The Hall Susceptibility or the measured current-in-plane resistance susceptibility can be measured at a frequency ranging from DC to 1 gigahertz (GHz), specifically from DC to 10 kilohertz (kHz). The phase sensitive measurement can have a bandwidth from 0.3 hertz (Hz) to 100 kilohertz (kHz), specifically from 1 Hz to 1 kHz, and more specifically from 10 Hz to 100 Hz. The primary field can have a magnetic field strength from 0.0001 Tesla to 0.1 Tesla, specifically from 0.0003 Tesla to 0.01 Tesla, and more specifically from 0.001 Tesla to 0.003 Tesla. The DC alternating current can have a magnitude from 0.0001 Ampere to 10 Amperes, specifically from 0.01 Ampere to 5 Amperes, and more specifically from 0.5 Ampere to 3 Amperes.

Additionally, a temperature of susceptometer 100 advantageously can have a selected measurement ambient temperature. The temperature can be adjusted from 150 Kelvin to 500 Kelvin, specifically from 250 Kelvin to 400 Kelvin, and more specifically from 260 Kelvin to 350 Kelvin.

Additionally, susceptometer 100 advantageously can have a selected material composition for significant electromagnetic noise reduction. In an embodiment where the material for sample chamber 104 and electrode chamber 106 is made of conducting materials such as copper, bronze, aluminum or the like, an electromagnetic shield is formed around electrodes 108 and sample 162, which is generally known to reduce electromagnetic interference and provide superior electromagnetic noise reduction when compared to non-metallic material shielding.

Susceptometer 100 has beneficial and advantageous uses. In an embodiment, a process for performing magnetic susceptometry on sample 162 includes: providing sample 162 to susceptometer 100, including: substrate 160; the plurality of electrodes 180, including: first pair 400 of electrodes disposed on substrate 160 and being electrically conductive to engage and be in electrical contact with sample 162; second pair 402 of electrodes disposed on substrate 160 and being electrically conductive to engage and be in electrical contact with sample 162, second pair 402 of electrodes arranged collinear with first pair 400 of electrodes to form set 408 of aligned electrodes; and third pair 404 of electrodes disposed on substrate 160 and being electrically conductive to engage and be in electrical contact with sample 162, third pair 404 of electrodes arranged noncollinearly with set 408 of aligned electrodes; and solenoid 166 circumscribingly disposed around electrodes 108; receiving sample 162 in solenoid 166 such that solenoid 166 is circumscribingly disposed around sample 162; providing solenoid 166 with an alternating current; producing, by solenoid, a primary magnetic field in response to receiving the alternating current; subjecting sample 162 to the primary magnetic field; and subjecting sample 162 to a direct current electrical current to perform magnetic susceptometry.

According to an embodiment, the process further includes measuring a Hall voltage of the sample.

According to an embodiment, the process further includes measuring a current-in-plane resistance of the sample.

Figure 49:
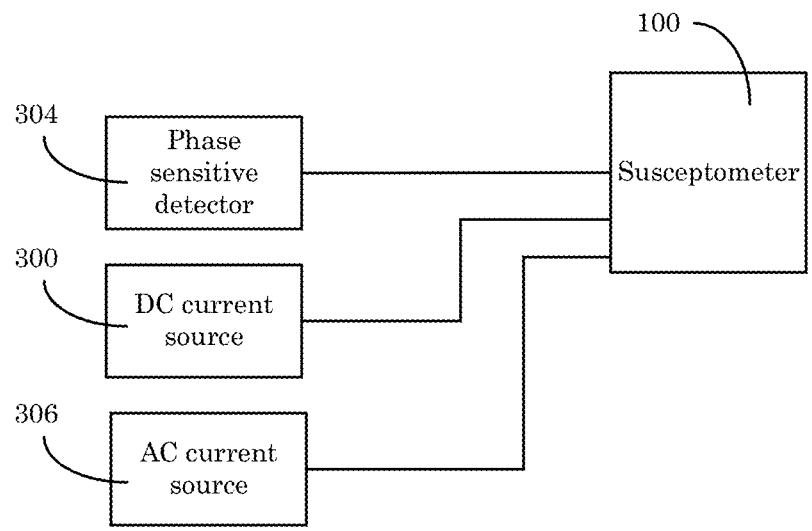
FIG. 49 shows a system.

Advantageously, in an embodiment, susceptometer 100 is included in system 400 for performing magnetic susceptometry. As shown in FIG. 49, system 400 includes susceptometer 100 in electrical communication with phase sensitive detector 304, DC current source 300, and AC current source 306. DC current source 300 provides electrical current to electrodes 108 of susceptometer 100 such that the Hall voltage of sample 162 or current-in-plane resistance of sample 162 is measured by system 400. AC current source 306 provides the alternating electrical current to solenoid 166 of susceptometer 100 and also provides the primary frequency (of the alternating electrical current provided to solenoid 166) to phase sensitive detector 304. Solenoid 166 produces the primary magnetic field in response to receiving the alternating electric current from AC current source 306. Sample 162 disposed in susceptometer 100, produces a voltage response in response to being subjected to the primary magnetic field from solenoid 166. Electrodes 108 of susceptometer 100 are in electrical contact with sample 162, phase sensitive detector 304, and DC current source 300. Phase sensitive detector 304 receives the primary frequency from AC current source 306 as a reference frequency and receives the voltage response of sample 162. In this manner, the AC Hall magnetic susceptibility or the AC current-in-plane resistance magnetic susceptibility of sample 162 is detected by phase sensitive detector 304. Phase sensitive detector 304 produces a DC voltage ("first data") that has an amplitude proportional to the voltage response received from sample 162. The first data is analyzed to determine the AC magnetic susceptibility or the AC Hall resistivity of sample 162. Analysis of the first data can include multiplication of the data by calibration factors proportional to the peak magnetic flux density of the primary magnetic field and the DC electric current and proportional to the magnetization density of sample 162.

Figure 50:
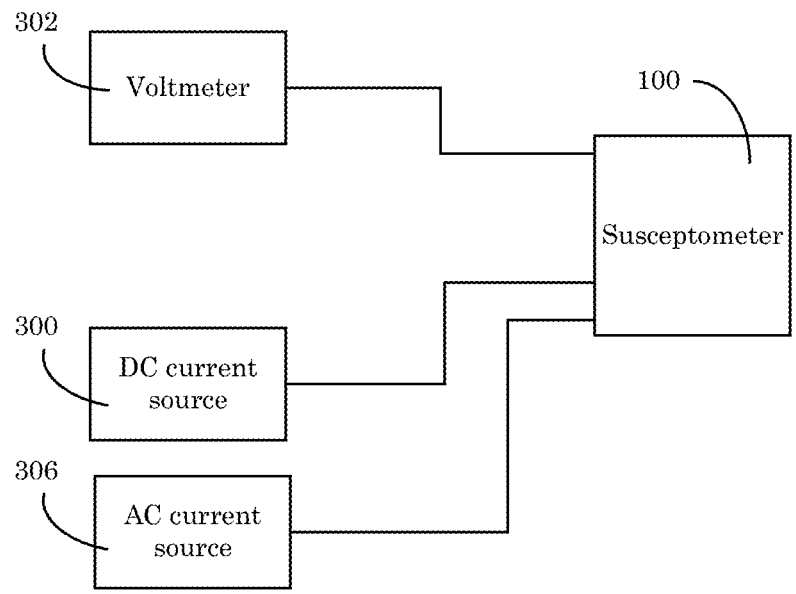
FIG. 50 shows a system.

In an embodiment, susceptometer 100 is included in system 400 for performing magnetic susceptometry. As shown in FIG. 50, system 400 includes susceptometer 100 in electrical communication with voltmeter 302, DC current source 300, and AC current source 306. DC current source 300 provides electrical current to electrodes 108 of susceptometer 100 such that the Hall voltage of sample 162 or current-in-plane resistance of sample 162 is measured by system 400. AC current source 306 provides the alternating electrical current to solenoid 166 of susceptometer 100. Solenoid 166 produces the primary magnetic field in response to receiving the alternating electric current from AC current source 306. Sample 162 disposed in susceptometer 100 produces a voltage response in response to being subjected to the primary magnetic field from solenoid 166. Electrodes 108 of susceptometer 100 are in electrical contact with sample 162, voltmeter 302, and DC current source 300. Voltmeter 302 receives the voltage response of sample 162 via electrodes 108. In this manner, the DC Hall Voltage or the DC current-in-plane resistance of sample 162 is detected by voltmeter 302. Voltmeter 302 produces a DC voltage ("second data"), e.g., by digitizing the analog voltage response received from electrodes 108 in contact with sample 162. The second data has an amplitude that is proportional to the voltage response received from sample 162. The second data is analyzed to determine the Hall Voltage or the current-in-plane resistance of sample 162. Analysis of the first data can include multiplication of the data by calibration factors proportional to the DC electric current and proportional to the magnetization density of sample 162.

Figure 51:
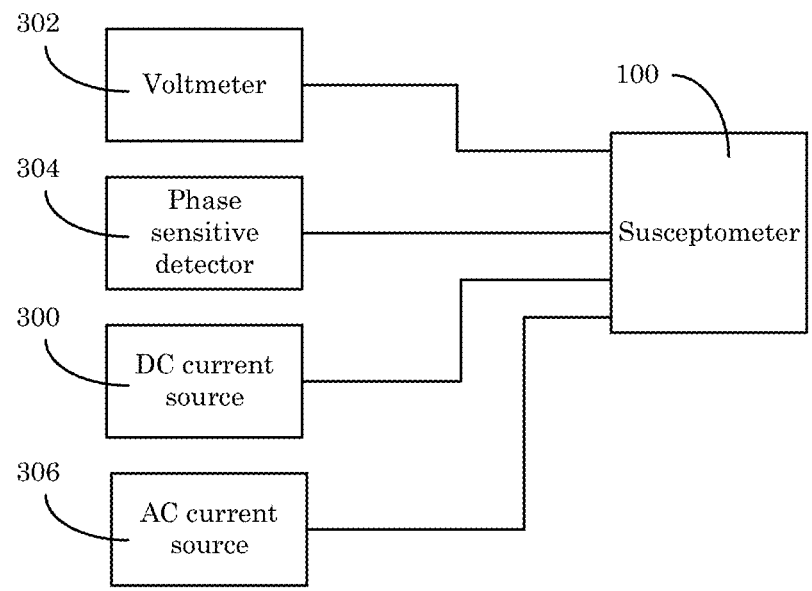
FIG. 51 shows a system.

In an embodiment, susceptometer 100 is included in system 400 for performing magnetic susceptometry. As shown in FIG. 51, system 400 includes susceptometer 100 in electrical communication with voltmeter 302, phase sensitive detector 304, DC current source 300, and AC current source 306. DC current source 300 provides electrical current to electrodes 108 of susceptometer 100 such that the Hall voltage of sample 162 or current-in-plane resistance of sample 162 is measured by system 400. AC current source 306 provides the alternating electrical current to solenoid 166 of susceptometer 100. Solenoid 166 produces the primary magnetic field in response to receiving the alternating electric current from AC current source 306. Sample 162 disposed in susceptometer 100 produces a voltage response in response to being subjected to the primary magnetic field from solenoid 166. Electrodes 108 are electrically reconfigurable in-situ and in contact with sample 162 to obtain reconfigurably the Hall voltage of sample 162 and the current-in-plane resistance of sample 162 while sample 162 is subjected to the DC electrical current from DC current source 300. That is, electrodes 108 can be electrically reconfigured in-situ while in contact with sample 162 between resistance configuration 290 and Hall voltage configuration 292 as shown respectively in FIG. 33 and FIG. 34 for electrodes 108 arranged as shown in FIG. 32, or electrodes 108 can be electrically reconfigured in-situ while in contact with sample 162 between resistance configuration 294 and Hall voltage configuration 296 as shown respectively in FIG. 36 and FIG. 37 for electrodes 108 arranged as shown in FIG. 35. Accordingly, electrodes 108 of susceptometer 100 are in electrical contact with sample 162 and can be selectively electrically reconfigured in-situ to be in electrical communication with voltmeter 302, phase sensitive detector 304, DC current source 300, or a combination thereof. When electrodes 108 are configured in Hall voltage configuration (e.g., 292 or 296), phase sensitive detector 304 receives the primary frequency from AC current source 306 as a reference frequency and receives the voltage response of sample 162. In this manner, the AC Hall susceptibility of sample 162 is detected by phase sensitive detector 304. Phase sensitive detector 304 produces the first data, and the first data can be analyzed to determine AC Hall resistivity of sample 162. Additionally, when electrodes 108 are configured in resistance configuration (e.g., 290 or 294), voltmeter 302 receives the voltage response of sample 162 via electrodes 108. In this manner, the AC current-in-plane resistance magnetic susceptibility of sample 162 is detected by voltmeter 302. Voltmeter 302 produces the second data, and the second data can be analyzed to determine AC magnetic susceptibility of sample 162.

Figure 52:
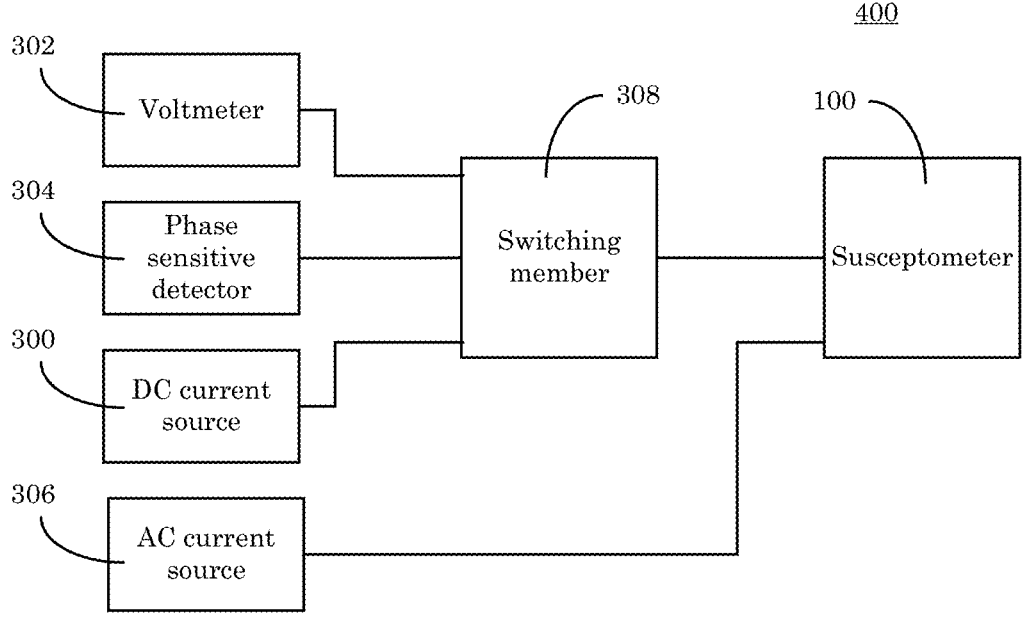
FIG. 52 shows a system.

In an embodiment, susceptometer 100 is included in system 400 for performing magnetic susceptometry. As shown in FIG. 52, system 400 includes susceptometer 100 in electrical communication with AC current source 306 and in switchable electrical communication with voltmeter 302, phase sensitive detector 304, and DC current source 300. Switching member 308 is electrically interposed between electrodes 108 of susceptometer 100 and voltmeter 302, phase sensitive detector 304, and DC current source 300 to selectively switch electrical communication between electrodes 108 and voltmeter 302, phase sensitive detector 304, and DC current source 300.

Switching member 308 can include a plurality of electro-mechanical switches that can reconfigure electrical connections between electrodes 108 of susceptometer 100 and voltmeter 302, phase sensitive detector 304 and DC current source 300. Exemplary switching members 308 include manually-actuated, single-pull double-throw switches; manually-actuated, single-pull single-throw switches; latching electromagnetic relays controlled by a computer-controlled microcontroller; and the like.

DC current source 300 provides electrical current to electrodes 108 of susceptometer 100 such that the Hall voltage of sample 162 or current-in-plane resistance of sample 162 is measured by system 400. AC current source 306 provides the alternating electrical current to solenoid 166 of susceptometer 100. Solenoid 166 produces the primary magnetic field in response to receiving the alternating electric current from AC current source 306. Sample 162 disposed in susceptometer 100 produces a voltage response in response to being subjected to the primary magnetic field from solenoid 166. Switching member 308 electrically reconfigures electrodes 108 in-situ (i.e., without physically removing electrodes 108 from chamber 102 of susceptometer 100 and without breaking electrical contact with sample 162) and in contact with sample 162 to obtain reconfigurably the Hall voltage of sample 162 and the current-in-plane resistance of sample 162 while sample 162 is subjected to the DC electrical current from DC current source 300. That is, electrodes 108 are electrically reconfigured in-situ by switching member 308 while electrodes 108 are in contact with sample 162 such that electrodes 108 are switched between resistance configuration 290 and Hall voltage configuration 292, as shown respectively in FIG. 33 and FIG. 34 for electrodes 108 arranged as shown in FIG. 32, or as shown in respectively in FIG. 36 and FIG. 37 for electrodes 108 arranged as shown in FIG. 35. Accordingly, electrodes 108 of susceptometer 100 are in electrical contact with sample 162 and can be selectively electrically reconfigured in-situ by switching member 308 to be in electrical communication with voltmeter 302, phase sensitive detector 304, DC current source 300, or a combination thereof. When electrodes 108 are configured in Hall voltage configuration (e.g., 292 or 296), phase sensitive detector 304 receives the primary frequency from AC current source 306 as a reference frequency and receives the voltage response of sample 162. In this manner, the AC Hall susceptibility of sample 162 is detected by phase sensitive detector 304. Phase sensitive detector 304 produces the first data, and the first data can be analyzed to determine AC Hall resistivity of sample 162. Additionally, when electrodes 108 are configured in resistance configuration (e.g., 290 or 294), voltmeter 302 receives the voltage response of sample 162 via electrodes 108. In this manner, the current-in-plane DC voltage of sample 162 is detected by voltmeter 302. Voltmeter 302 produces the second data, and the second data can be analyzed to determine the current-in-plane DC resistance of sample 162.

Figure 53:
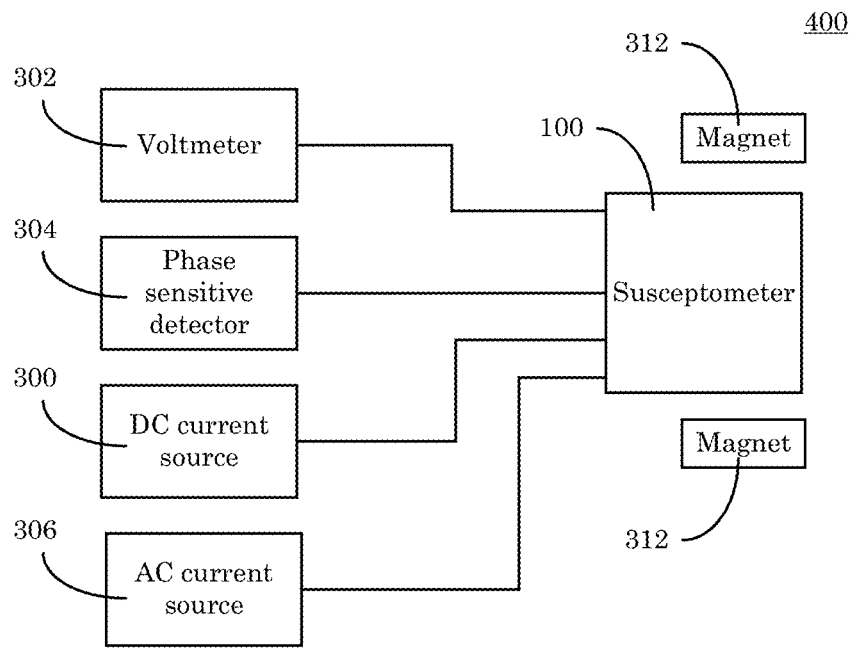
FIG. 53 shows a system.

In an embodiment, as shown in FIG. 53, system 400 includes magnet 312 disposed proximate to susceptometer 100 to provide a secondary magnetic field to sample 162 disposed in susceptometer 100. Magnetic field lines of the secondary magnetic field can be aligned with magnetic field lines of the primary magnetic field produced by solenoid 166. In an embodiment, magnetic field lines of the secondary magnetic field are not aligned with magnetic field lines of the primary magnetic field produced by solenoid 166. The secondary magnetic field can be static or can vary in time. A field strength of the secondary magnetic field can be from 0.5 milliTesla (mT) to 2 Tesla, specifically from 3 milliTesla (mT) to 500 mT, and more specifically from 10 milliTesla (mT) to 200 mT. Magnet 312 can be a permanent magnet or an electromagnet. Magnet 312 can include a plurality of pole pieces having a selected shape. In an environment, magnet 312 is the electromagnet. The electromagnet can be in electrical communication with a power source to control production of secondary magnetic field by magnet 312, a field strength of the secondary magnetic field, a temporal variation of the secondary magnetic field, and the like.

Figure 54:
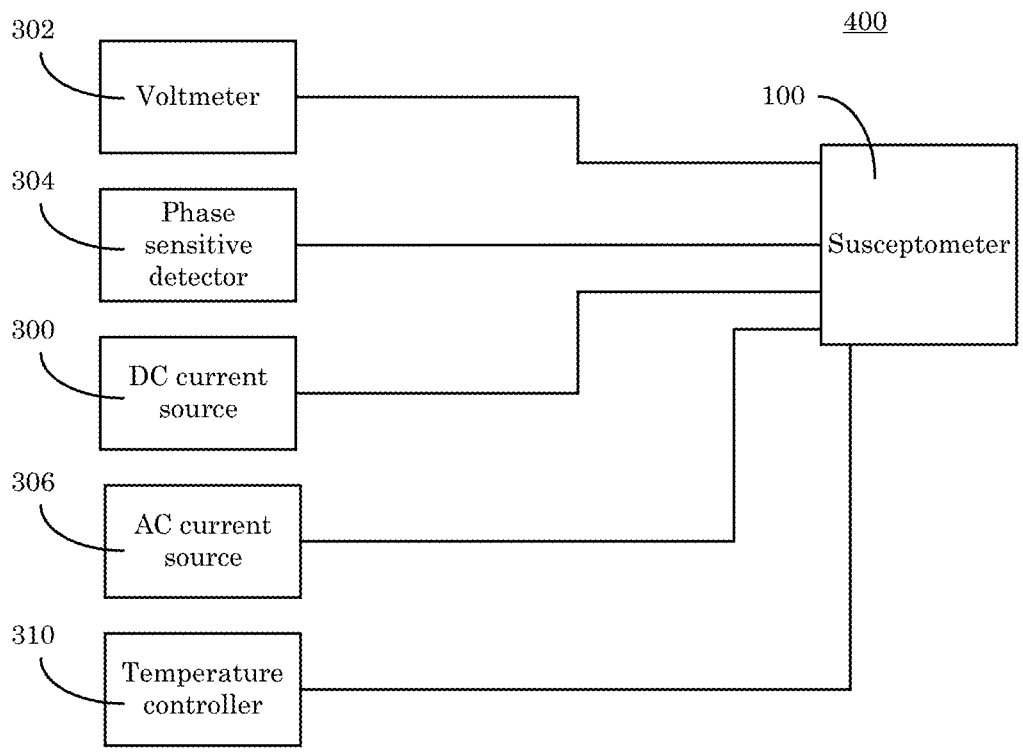
FIG. 54 shows a system.

In an embodiment, as shown in FIG. 54, system 400 includes temperature controller 310 in electrical communication (or thermal communication) with a thermal member disposed in sample chamber 106 of susceptometer 100. Here, thermal member controls a temperature of sample 162 disposed in susceptometer 100. Temperature controller 310 controls a temperature of the thermal member. Temperature controller 310, e.g., can be a converter that digitizes a calibrated voltage signal proportional to the temperature measured at the location of the thermal member disposed in sample chamber 106, and includes a feedback algorithm to regulate the heating/cooling power of the thermal member disposed in sample chamber 106.

Figure 55:
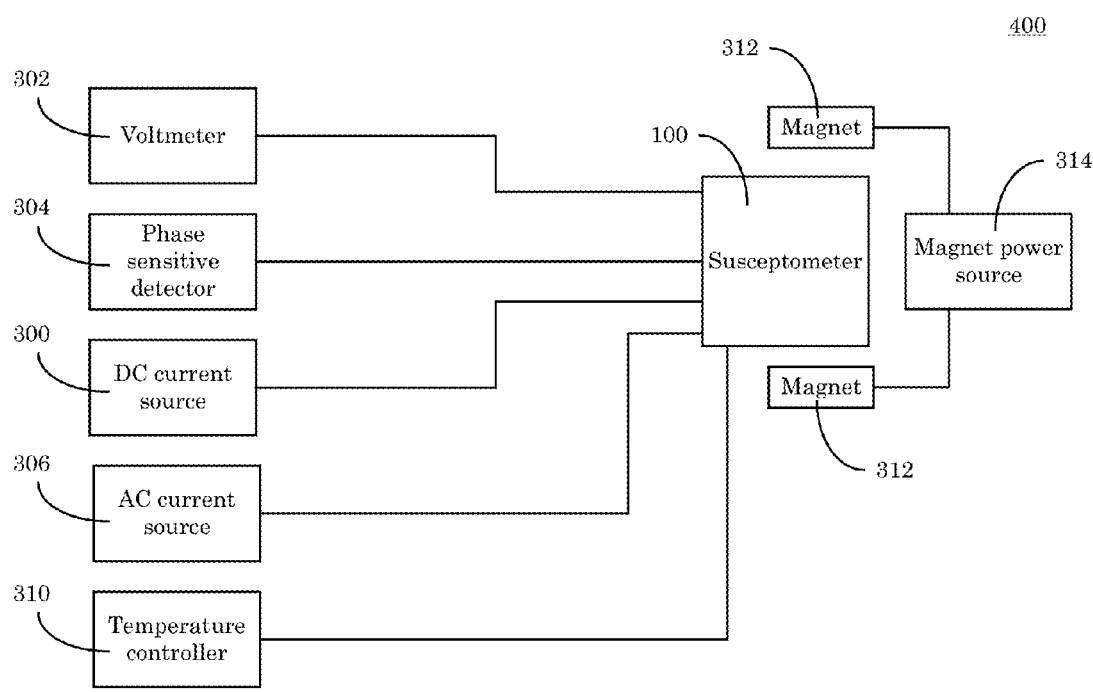
FIG. 55 shows a system.

In an embodiment, as shown in FIG. 55, system 400 includes temperature controller 310 in electrical communication (or thermal communication) with a thermal member disposed in sample chamber 106 of susceptometer 100, magnet 312, and magnet power source 314 in electrical communication with magnet 312.

Figure 56:
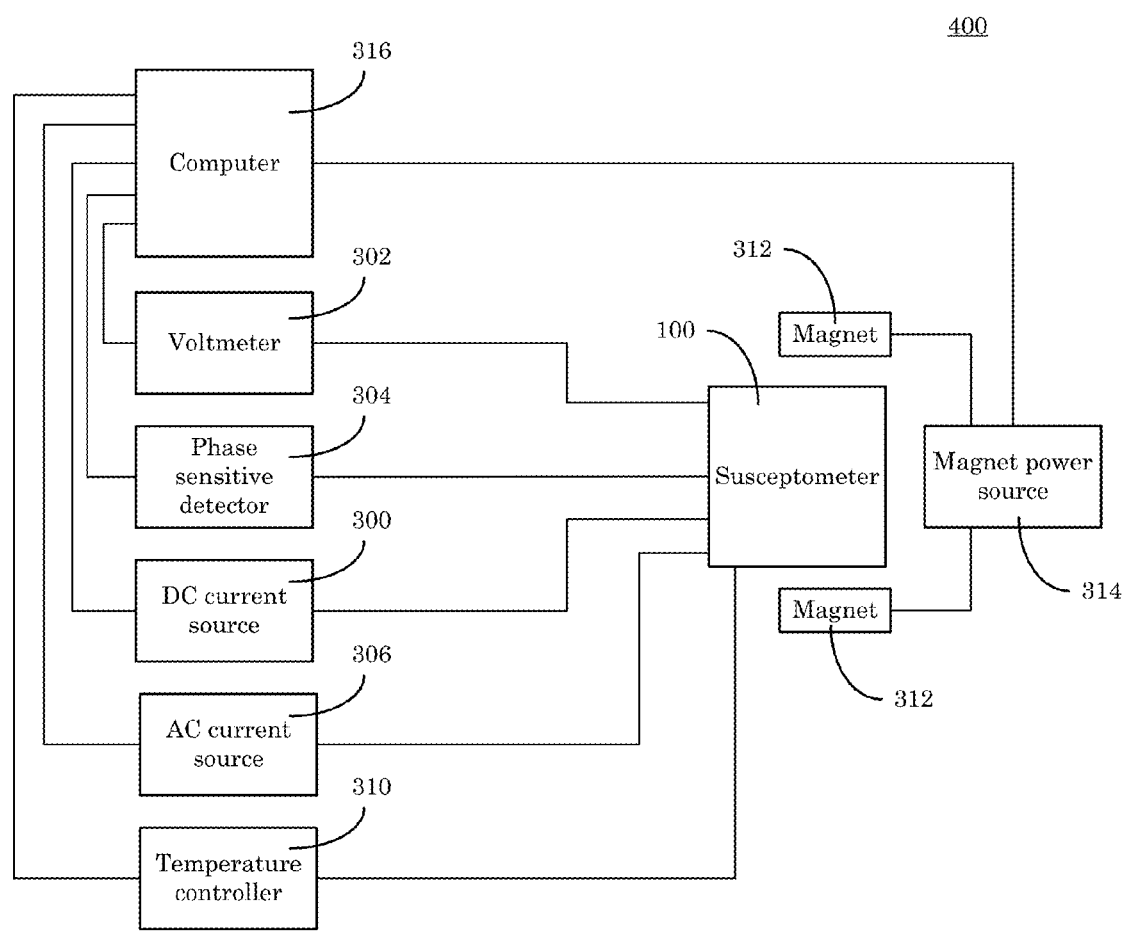
FIG. 56 shows a system.

In an embodiment, as shown in FIG. 56, system 400 includes computer 316 in communication with various components of system 400 to control the various components or to acquire data from the various components.

Figure 57:
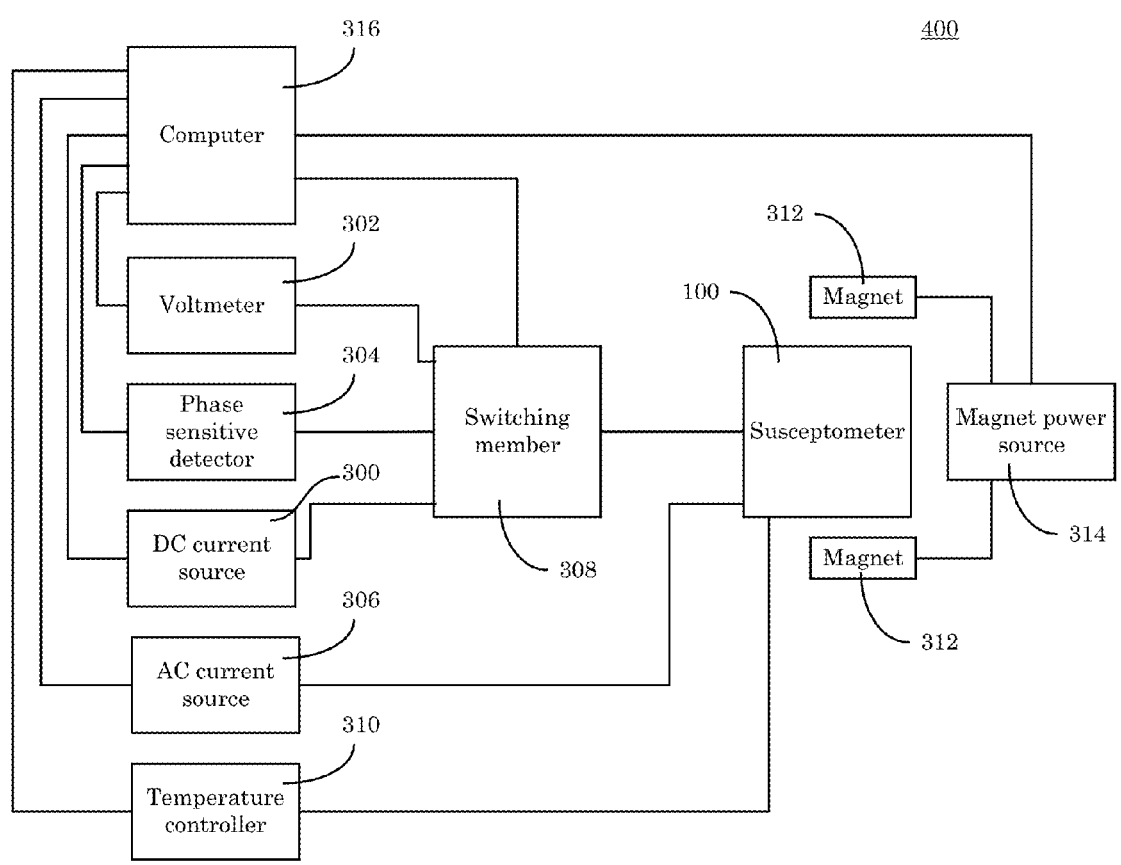
FIG. 57 shows a system.

In an embodiment, as shown in FIG. 57, system 400 includes computer 316 in communication with various components (e.g., switching member 308) of system 400 to control the various components or to acquire data from the various components.

Figure 58:
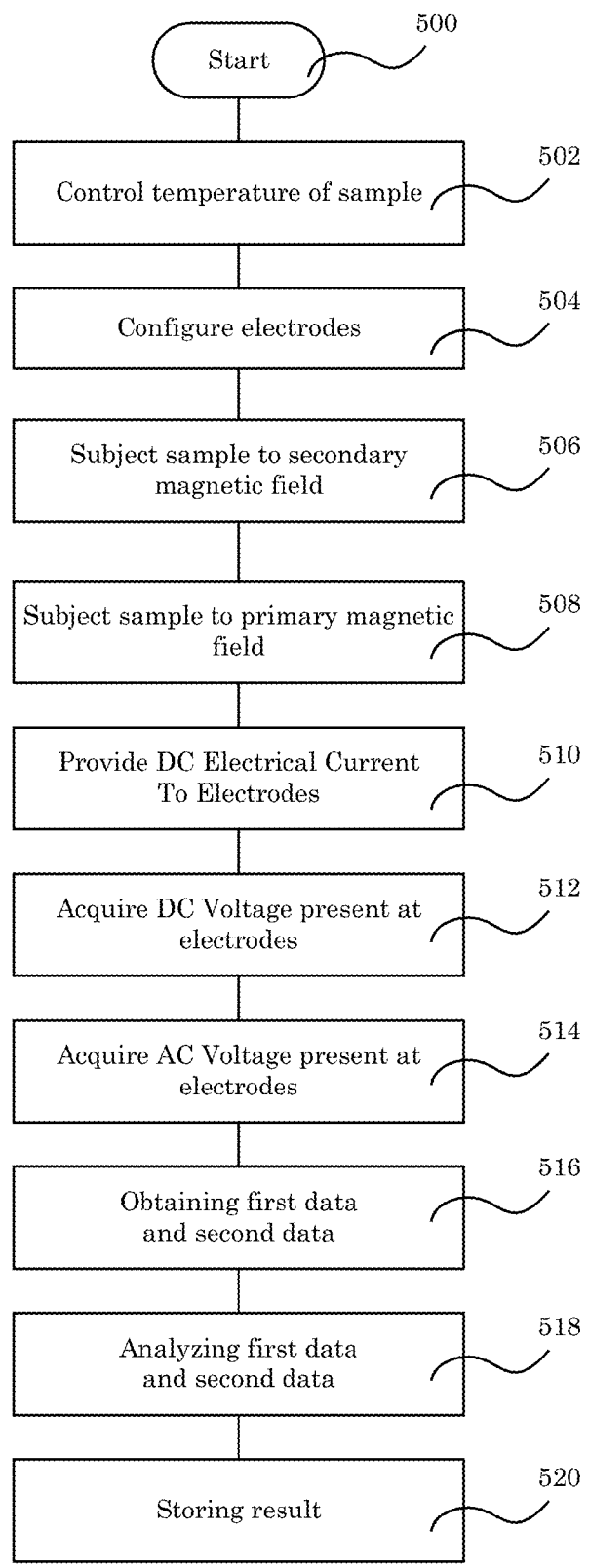
FIG. 58 shows a flowchart for performing magnetic susceptometry.

In an embodiment, system 400 (e.g., as shown in FIG. 49, FIG. 50, FIG. 51, FIG. 52, FIG. 53, FIG. 54, FIG. 55, FIG. 56, FIG. 57, and the like) include susceptometer 100 and is configured to perform magnetic susceptometry on sample 162 disposed in susceptometer 100. With reference to FIG. 58, the process for performing magnetic susceptometry on sample 162 includes providing sample 162 in susceptometer 100 (step 500), controlling the temperature of sample 162 (step 502), configuring electrodes 108 (step 504), subjecting sample 162 to the secondary magnetic field produced by magnet 312 (step 506), subjecting sample 162 to the primary magnetic field produced by solenoid 166 (step 508), providing DC electrical current from DC current source 300 to electrodes 108 (step 510), acquiring DC voltage present at electrodes 108 by voltmeter 302 (step 512), acquiring AC voltage present at electrodes 108 by phase sensitive detector 304 that is referenced to the primary frequency produced by AC current source 306 (step 514), communicating the second data from voltmeter 302 and first data from phase sensitive detector 304 to computer 316 (step 516), analyzing first and second data (e.g., first data or second data by a calibration data) (step 518) to obtain DC Hall Voltage, DC Current-in-plane Resistance, AC Hall Susceptibility and AC Current-in-plane Magnetic Susceptibility, and optionally communicating the aforementioned to an output device or storage medium.

Susceptometer 100 provides beneficial and advantages uses. Susceptometer 100 can be used as a digitally configurable susceptometer. In an embodiment, susceptometer 100 is a digitally configurable susceptometer based, e.g., on a semiconducting or magnetoelectronic effect. Susceptometer 100 provides measurements of steady-state (DC) voltage response (U) of sample 100, e.g., the thin film, subjected to an static applied magnetic field (B) provided by the secondary magnetic field or a differential voltage response ($\Delta$U) to the primary magnetic field provided by a solenoid 166 having an excitation field ($\Delta$B) at selected primary frequency f.

Sample 162 can include a semiconducting thin film, ferromagnetic thin film with perpendicular-to-the-plane magnetization, an anomalous magnetoresistance thin film, a giant magnetoresistance thin film, or a combination thereof. A complex signal from sample 162 can be obtained by susceptometer 100, which can be accomplished e.g., by disposing a ferromagnetic thin film in susceptometer 100 disposed within the secondary magnetic field from magnet 312. Here, the Hall Voltage versus applied DC field and differential Hall Susceptibility (dV/dB) versus applied DC field are determined from a response of sample 162 acquired by susceptometer 100, e.g., in system 400. As a result, analysis of such data provides determination of a demagnetization curve of the ferromagnetic film or a magnetic susceptibility.

Advantageously, in an embodiment, susceptometer 100 isolates an interference response from a desired magnetic response from sample 162. Here, a time-varying primary magnetic field is produced by solenoid 166 to induce a transient Hall voltage in phase with the primary magnetic field, and the signal obtained by susceptometer 100 from sample 162 is the Hall susceptibility for sample 162. The Hall susceptibility is the differential Hall voltage response ($\Delta$U) to the alternating field ($\Delta$B) of the primary magnetic field produced by solenoid 166.

Beneficially, susceptometer 100 provides complex measurements or determination of susceptibility of a ferromagnetic thin film (that also relate to the homogeneity of magnetic properties in sample 162). Susceptometer 100 also provides robust and time saving mechanical mounting of sample 162 inside chamber 102 and electrode 108 (e.g., spring loaded pins) disposition via electrode chamber 104. Disposition of the heater also provides thermal control of sample 162 and components of chamber 102.

Susceptometer 100 attains first data and second data that are analyzed to obtain a magnetic property or a semiconducting property of sample 162 that was subjected to the primary magnetic field at an operating temperature of a semiconductor chip, e.g., an elevated temperature such as 80° C. Susceptometer 100 also provides electrical reconfiguration of electrodes 108 between Hall voltage configuration, and resistance configuration. Accordingly, susceptometer 100 measures a plurality of properties of samples 162 that include semiconducting and magnetic thin films. In an embodiment, susceptometer 100 measures an electrical or magnetoelectronic property of sample 162. In an embodiment, susceptometer 100 measures an electrical property or magnetoelectronic property of sample 162 by subjecting sample 162 to an AC magnetic field, DC magnetic field, or combination thereof.

In an embodiment, susceptometer 100 measures an AC or DC electrical property or magnetoelectronic property of sample 162. Exemplary electrical properties of sample 162 include DC or AC ordinary Hall Effects, 4-point in-line resistance, DC van der Pauw resistivity, and the like. Exemplary magnetoelectronic properties of sample 162 include mean AC magnetic susceptibility, AC or DC Hall (planar or extraordinary), AC or DC current-in-plane giant magnetoresistance, and the like. AC measurements of sample 162 are produced by susceptometer 100 using near field magnetic excitation from solenoid 162 disposed proximate to sample 162.

Susceptometer 100 advantageously provides calibration for AC measurements which can be calculated easily from consideration of geometry of the coil and proximity to a sample under test. Here, the AC current passing through the solenoid coil is calibrated by the voltage difference between the leads of a low-impedance resistor (for example, a 1 Ohm power resistor) connected serially to the solenoid coil. Then, using equations that describe the magnetic field produced by current carrying wires, we can estimate the AC magnetic field produced at the location of sample 162 undergoing susceptometry. The measured AC Hall Susceptibility or Current-in-plane Susceptibility is the product of the root-mean-square of the AC magnetic field times the Susceptibility, and thus the measured quantities must be divided by the calibrated AC magnetic field in order to realize a calibrated value for the AC Hall Susceptibility or the AC Current-in-plane Susceptibility.

Susceptometer 100 advantageously provides use within an electromagnet for AC measurement of magnetic susceptibility during remagnetization of sample 162 to obtain first order reversal curves; AC excitation field over a wide range of magnitudes (e.g., 80 Am$^{-1}$ (1 Oe) to 8000 Am$^{-1}$ (100 Oe) peak amplitude) and frequencies (0.1 Hz to 10 kHz).

Susceptometer 100 advantageously provides control of AC excitation field amplitude and frequency to perform direct testing, e.g., of magnetic field sensor signal-to-noise ratios over decades of frequency.

Susceptometer 100 advantageously provides measurement of harmonic susceptibilities (e.g., anomalous magnetoresistance susceptibility at double the near field excitation frequency), AC or DC resistances, and Hall Effect (e.g., planar, ordinary, extraordinary Hall Effect; anomalous magnetoresistance; giant magnetoresistance, and the like).

Susceptometer 100 advantageously provides automation and unattended operation with automated control for a selected research or experimental protocol.

Susceptometer 100 advantageously receives sample 162 that can include a thin film that has a ferromagnetic or semiconducting property, including a spintronic multilayer, ferromagnetic layer, semiconductor, thin film recording media, and the like. Furthermore, susceptometer 100 advantageously provides reconfigurable electrodes 108 for AC or DC measurements of sample 162 as well as in-line or transverse electrical measurements of sample 162.

First data and second data obtained from susceptometer 100 can be analyzed as follows. The primary magnetic field produced by solenoid 166 has a time-varying magnetic field strength and direction, wherein the field strength is provided in formula 1.

$$\vec{B} = (0, 0, B_0 \cos \omega t) \quad (1)$$

The current density j flowing along a length L (along X-axis) of sample 162 is provided in formula 2.

$$\vec{J} = (j, 0, 0); I = j * L * W * T, \quad (2)$$

Here, I represents the direct current flowing through sample 162, and L, W and T are the length, width, and thickness of sample 162. The magnetization of sample 162 is provided in formula 3.

$$\vec{m} = (m_x, m_y, m_z); |\vec{m}| = 1 \quad (3)$$

Sample 162 can be a giant magnetoresistance sensor, which includes a first magnetic layer disposed on a second magnetic layer. A magnetization orientation $m_p$ of the second magnetic layer is fixed along the Z-axis and provided in formula 4.

$$\vec{m}_p = (0, 0, m_p); |\vec{m}_p| = 1 \quad (4)$$

Because of the current flowing along the X-axis of sample 162, voltages develop longitudinally (parallel to current flow in sample 162) and transversally (orthogonal to current flow in sample 162). The longitudinal voltage $V_\parallel$ and the Hall voltage $V_\perp$ are measured by susceptometer 100. The longitudinal voltage has four main terms and is provided in formula 5.

$$V_\parallel = V \| j = I R_\parallel + j L \rho_\perp^m + j L \Delta \rho^m \left( \vec{m} \cdot \frac{\vec{J}}{|\vec{J}|} \right)^2 + \frac{I \Delta GMR}{2} (1 - \vec{m} \cdot \vec{m}_p) \quad (5)$$

Here, $\Delta \rho^m = \rho_\parallel^m - \rho_\perp^m$ Term 1 ($IR_\parallel$) corresponds to an Ohmic voltage drop across the resistance ($R_\parallel$) of sample 162 along the direction of current flow. Terms 2 and 3

$$\left( j L \rho_\perp^m + j L \Delta \rho^m \left( \vec{m} \cdot \frac{\vec{J}}{|\vec{J}|} \right)^2 \right)$$

identify an anisotropic magnetoresistance present in a ferromagnetic material and reflect a change in a resistivity of a sample for current flowing parallel ($\rho_\parallel^m$) versus orthogonal ($\rho_\perp^m$) to the magnetization orientation of the sample. Term $$4 \left( \frac{I \Delta GMR}{2} (1 - \vec{m} \cdot \vec{m}_p) \right)$$

is present in a giant magnetoresistance sensor and is a change in resistance ($\Delta GMR$) due to relative misorientation of the first and second ferromagnetic layers, which are $\vec{m}$ and $\vec{m}_p$.

The Hall voltage is provided in formula 6.

$$V_\perp = V \perp j, B = I R_H B_0 \cos \omega t + I R_{EHE} m_z \quad (6)$$

Here, term 1 ($IR_H B_0 \cos \omega t$) is the ordinary Hall Effect; $R_H$ is the Hall resistance ($-1/nTe$); n is charge carrier density of sample 162; T is the thickness, and e is the elementary electron charge. Term 2 ($IR_{EHE} m_z$) is the extraordinary (also referred to as anomalous) Hall Effect voltage and is proportional to the Z-component of the magnetization of sample 162. Term 2 is present in magnetic materials and can be greater than Term 1. The Hall Voltage in a ferromagnet serves as a proxy for the Z-component of magnetization and can be used to measure the magnetization.

Solenoid 166 excites semiconducting and ferromagnetic responses in the longitudinal and Hall voltage configurations. Here, the sample can be a ferromagnetic film with a magnetization substantially oriented within the X-Y plane, which has a nearly linear magnetic susceptibility ($\chi_{zz}$) on the z-component of magnetization ($m_z$) to magnetic fields ($B_z$) in the z-direction as provided in formula 7.

$$m_z << m_x, m_y; m_z \cong \chi_{zz} B_z \quad (7)$$

The in-plane magnetization is provided in formula 8.

$$m_x = m_y = \sqrt{1 - m_z^2} \cong 1 - \frac{m_z^2}{2} = 1 - \frac{1}{2}\chi_{zz}^2 B_z^2 \quad (8)$$

In assuming that the magnetization is oriented along the X-axis or along the Y-axis, deviations due to applied fields along the Z-axis are linearly proportional to the field through the magnetic susceptibility.

Formula 9 provides the time-dependent longitudinal voltage response of formula 5 for a thin film sample under DC current I, and near field excitation B with magnetization m and part of a giant magnetoresistance sensor with pinned magnetization $m_p$.

$$\begin{aligned} V_\parallel(t) &= IR_\parallel + jL\rho_\perp^m + jL\Delta\rho^m m_y^2 + \frac{I\Delta GMR}{2}(1 - m_z) \\ &= IR_\parallel + jL\rho_\perp^m + jL\Delta\rho^m\left(1 - \frac{1}{2}\chi_{zz}^2 B_z^2\right)^2 + \frac{I\Delta GMR}{2}(1 - \chi_{zz}B_z) \\ &= IR_\parallel + jL\rho_\parallel^m + jL\chi_{zz}^2 B_0^2 \Delta\rho^m \cos^2\omega t + \\ &\quad \frac{jL}{4}\chi_{zz}^4 B_0^4 \Delta\rho^m \cos^4 \omega t + \frac{I\Delta GMR}{2}(1 - \chi_{zz}B_0\cos\omega t) \\ &= IR_\parallel + jL\rho_\parallel^m - \frac{jL}{2}\chi_{zz}^2 B_0^2 \Delta\rho^m - \frac{jL}{2}\chi_{zz}^2 B_0^2 \Delta\rho^m \cos 2\omega t + \\ &\quad \frac{3jL}{32}\chi_{zz}^4 B_0^4 \Delta\rho^m + \frac{jL}{8}\chi_{zz}^4 B_0^4 \Delta\rho^m \cos 2\omega t + \\ &\quad \frac{jL}{32}\chi_{zz}^4 B_0^4 \Delta\rho^m \cos 4\omega t + \frac{I\Delta GMR}{2} - \frac{I\Delta GMR}{2}\chi_{zz}B_0 \cos 2\omega t \end{aligned} \quad (9)$$

The time-dependent Hall voltage response of formula 6 is provided in formula 10.

$$V_\perp = IR_H B_0 \cos \omega t + IR_{EHE} m_z = IR_H B_0 \cos \omega t + IR_{EHE}\chi_{zz} B_0 \cos \omega t \quad (10)$$

Susceptometer 100 can measure harmonic and static responses of sample 162 according to formula 9 and formula 10. The DC longitudinal response of sample 162 is provided in formula 11.

$$V_\parallel^{DC} = IR_\parallel + jL\rho_\parallel^m - \frac{jL}{2}\chi_{zz}^2 B_0^2 \Delta\rho^m \left(1 - \frac{3}{16}\chi_{zz}^2 B_0^2\right) + \frac{1}{2}I\Delta GMR \quad (11)$$

Formula 11 includes four terms, and term (1) is the DC resistance parallel to the current flow in sample 162 and is present in a sample that is thin film. Term (2) is a DC effect due to the anomalous magnetoresistance (AMR) response of a ferromagnetic thin film due to current flow parallel to the magnetization. Term (3) is due to the AMR effect and to a rectification of the oscillating magnetization in response to the excitation field ($\chi_{zz}B_0 \cos \omega t$) as the magnetization factors into the AMR effect as the square ($m^2$), which provide terms that scale as $(\cos \omega t)^2$ and $(\cos \omega t)^4$. Term (4) is due to the giant magnetoresistance effect. In a sample in which a magnetic layer is absent (i.e., a sample without any magnetic layer), term (1) is present, and the other terms are absent in formula 11. In samples with only a single magnetic layer, terms (1-3) are present in formula 11. In a giant magnetoresistance sensor, all four terms are present at DC in formula 11.

A time-varying response is present at the near-field excitation frequency $\omega$ as provided in formula 12.

$$V_\parallel^\omega = -\frac{I\Delta GMR}{2}\chi_{zz}B_0 \quad (12)$$

The response is due to the giant magnetoresistance of sample 162. If sample 162 has all four terms at DC as in formula 11, and the current-in-plane resistance susceptibility is measured by phase sensitive detector 304 at a reference frequency of the fundamental frequency $\omega$, the giant magnetoresistance contribution to this measurement is isolated.

Harmonic terms at $2\omega$ and at $4\omega$ are provided in formula 13 and formula 14.

$$V_\parallel^{2\omega} = -\frac{jL}{2}\chi_{zz}^2 B_0^2 \Delta\rho^m \left(1 - \frac{1}{4}\chi_{zz}^2 B_0^2\right) \quad (13)$$

$$V_\parallel^{4\omega} = \frac{jL}{32}\chi_{zz}^4 B_0^4 \Delta\rho^m \quad (14)$$

Formula 13 and formula 14 show the AMR contribution at 2$\omega$ and 4$\omega$ can be measured using harmonic detection of phase sensitive detector 304. Measuring both harmonic frequencies provides the susceptibility ($\chi_{zz}$) and change in resistivity with magnetization orientation ($\Delta\rho_m$) of sample 162. For an AMR sensor, a greater susceptibility can mean more sensitivity to smaller magnetic fields. Harmonic effects are present for ferromagnetic samples, and samples with an AMR effect.

With respect to the Hall voltage response, the DC response is due to the Extraordinary Hall Effect provided in formula 15.

$$V_\perp^{DC} = IR_{EHE} m_z \quad (15)$$

Formula 15 provides normal-to-the-plane magnetization of a thin magnetic film. The signal at ($\omega$) is composed of both ordinary and extraordinary Hall Effect contributions is provided in formula 16.

$$V_\perp^\omega = IB_0(R_H + R_{EHE}\chi_{zz}) \quad (1)$$

In a non-magnetic, semiconducting sample, either $V_{DC}$ (as in formula 15) or $V^\omega$ (as in formula 16) is determined.

In accordance with formula 16, susceptometer 100 provides direct measurement of the Hall resistance at the fundamental frequency. Consequently, a static DC electromagnet can be absent in system 400 for standard Hall Effect measurements. Furthermore, susceptometer 100 provides the benefit of measuring the Hall voltage at a frequency where the signal-to-noise ratio is relatively lower than at DC. For a metallic ferromagnet sample, the Hall magnetic susceptibility is determined, which provides the magnetic sensitivity of sample 162.

The articles and processes herein are illustrated further by the following Example, which is non-limiting.

Example

A sample was prepared as a ferromagnetic film and was formed by physical vapor deposition. The film included a plurality of alternating layers of cobalt/platinum grown on a 1 cm$^2$ by 0.03 cm thick silicon wafer. The film had an extraordinary Hall Effect (EHE) voltage that was proportional to the magnetization aligned perpendicular to the film surface. Using a soluble resin, the sample was semi-permanently affixed to sample platform 178 and mounted to spool 164 in susceptometer 100. Susceptometer 100 was affixed to receiver 212 using couplers 202, 204 and 206, whereby receiver 212 was affixed to a track at a distance from the track floor so as to center and align susceptometer 100 with the midline of secondary magnet 312. The susceptometer 100 was rotated about the z-axis, as shown in FIGS. 2,3, in order to align the magnetic fields produced by primary solenoid coil 166 and secondary magnet 312.

Due to the EHE, the electrodes of the susceptometer were configured to measure the Hall voltage. Here, current was applied to a pair of electrodes (142 and 148, in configuration 296, FIG. 37), and voltage was measured between electrodes that were arranged diagonally to the first pair of electrodes (144 and 146, in configuration 296, FIG. 37). The magnetic field of the primary magnetic field produced by the solenoid of the susceptometer was applied perpendicular to the surface of the sample that was in contact with the electrodes. The primary magnetic field changed the perpendicular magnetization of the sample, and the change in EHE voltage was acquired via the electrodes. The sample was subjected continuously to the primary magnetic field. The primary magnetic field was a sine wave excitation at a frequency of 170 Hz and had a peak amplitude of 0.003 Tesla (2.4 kA/m).

Figure 59:
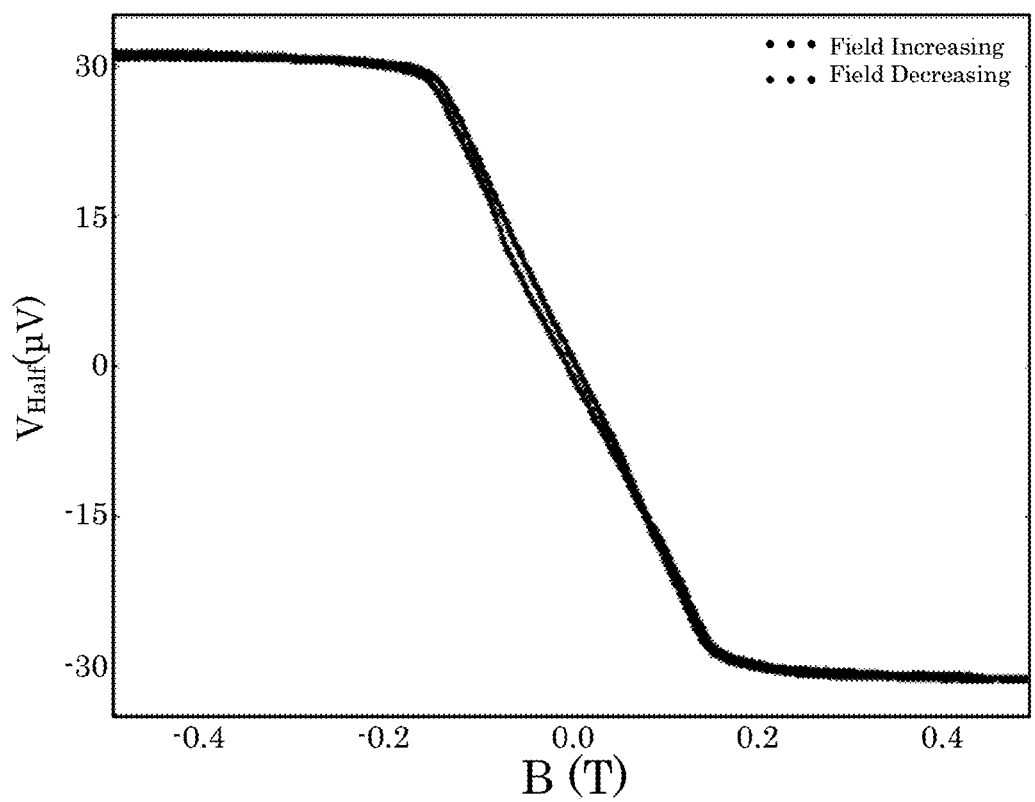
FIG. 59 shows a graph of Hall voltage versus magnetic field strength (also referred to as DC Hall magnetization) according to the Example.
Figure 60:
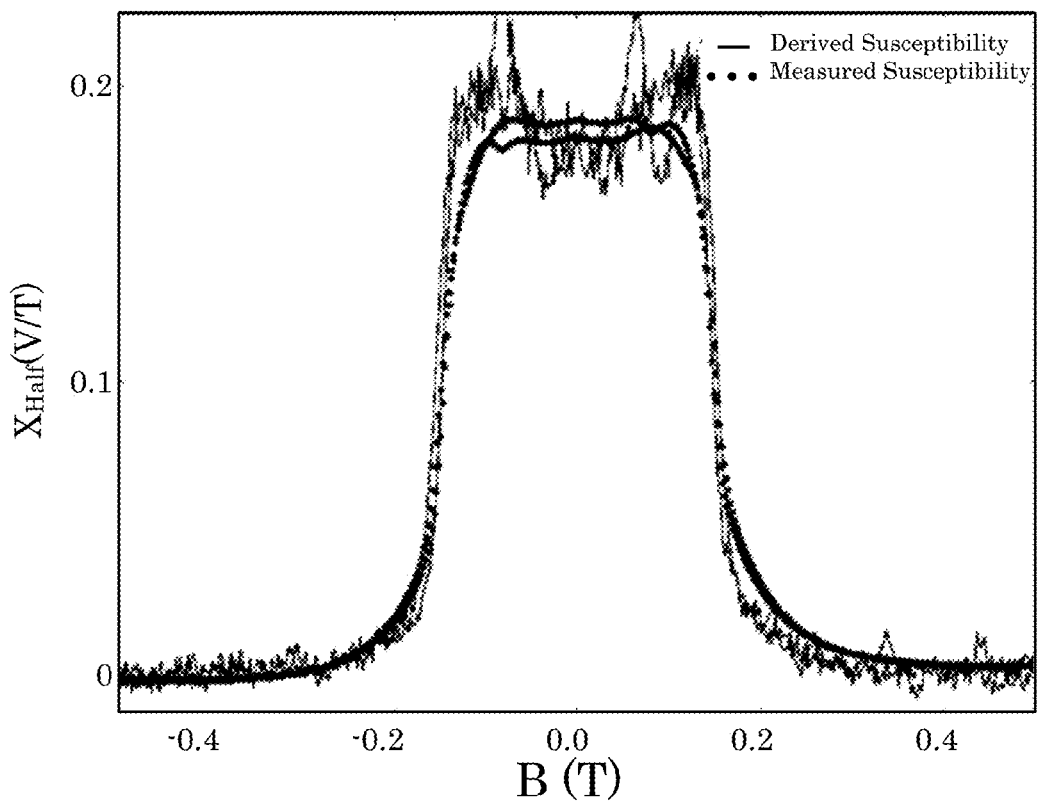
FIG. 60 shows a graph of susceptibility versus magnetic field strength (also referred to as AC Hall susceptibility) for data that was acquired simultaneously with the DC Hall magnetization data shown in FIG. 59.

With reference to FIG. 59, the graph shows Hall voltage versus applied perpendicular dc magnetic field strength of the primary magnetic field. The Hall voltage versus applied magnetic field strength of the primary magnetic field was nearly linearly. FIG. 60 shows a graph of susceptibility versus magnetic field strength (also referred to as AC Hall susceptibility) for data that was acquired simultaneously with the DC Hall magnetization data shown in FIG. 59. That is, the Hall Susceptibility is plotted versus applied perpendicular dc magnetic field. The magnetization of the sample followed the varying excitation field that provided a determination of dM/dB that followed the sinusoidal amplitude of the excitation field. When the sample was saturated, the susceptibility was zero, and when the applied dc magnetic field was small, the susceptibility was nearly constant. The data indicated a linear dependence of the perpendicular magnetization on perpendicular applied dc magnetic field.

Measurements of the sample were performed as the DC magnetic field applied perpendicular to the plane of the contact pins was applied step-wise from negative 0.5 Tesla (−400 kA/m) to positive 0.5 Tesla (+400 kA/m) and back with a 0.002 Tesla (1.6 kA/m) step increment. An AC magnetic field (also applied perpendicular to the plane of the contact pins) was applied continuously during this DC field sequence at a frequency of 170 Hz and a peak amplitude of 0.003 Tesla (2.4 kA/m). At each field step, the Hall voltage was measured using a digitizing voltmeter and a lock-in amplifier.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

Reference throughout this specification to "one embodiment," "particular embodiment," "certain embodiment," "an embodiment," or the like means that a particular feature, structure, or characteristic described in connection with the embodiment is included in at least one embodiment. Thus, appearances of these phrases (e.g., "in one embodiment" or "in an embodiment") throughout this specification are not necessarily all referring to the same embodiment, but may. Furthermore, particular features, structures, or characteristics may be combined in any suitable manner, as would be apparent to one of ordinary skill in the art from this disclosure, in one or more embodiments.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements, optionally together with one or more of the same class of constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." Further, the conjunction "or" is used to link objects of a list or alternatives and is not disjunctive; rather the elements can be used separately or can be combined together under appropriate circumstances. It should further be noted that the terms "first," "second," "primary," "secondary," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

What is claimed is:

1. A susceptometer comprising:
    a substrate;
    a plurality of electrodes to:
        subject a sample to a direct current electrical current; and
        measure at least one of a Hall voltage of the sample or a current-in-plane resistance of the sample,
    the plurality of electrodes comprising:
        a first pair of electrodes disposed on the substrate and being electrically conductive to engage and be in electrical contact with the sample;
        a second pair of electrodes disposed on the substrate and being electrically conductive to engage and be in electrical contact with the sample, the second pair of electrodes arranged collinear with the first pair of electrodes to form a set of aligned electrodes; and
        a third pair of electrodes disposed on the substrate and being electrically conductive to engage and be in electrical contact with the sample, the third pair of electrodes arranged noncollinearly with the set
of aligned electrodes; and
a solenoid circumscribingly disposed around the electrodes to:
receive the sample such that the solenoid is circumscribingly disposed around the sample;
receive an alternating current and produce a primary magnetic field based on the alternating current; and
subject the sample to the primary magnetic field.

2. The susceptometer of claim 1, further comprising a magnet disposed proximate to the electrodes and the solenoid to provide a secondary magnetic field to the sample,
wherein the magnet is disposed external to the solenoid.

3. The susceptometer of claim 1, further comprising a heater to heat the sample, the heater disposed proximate to the sample.

4. The susceptometer of claim 1, further comprising a switching member to switch the pairs of electrodes between a resistance configuration and a Hall voltage configuration,
wherein the switching member is in electrical communication with the plurality of electrodes.

5. The susceptometer of claim 1, further comprising a phase sensitive detector to detect a voltage response of the sample that is produced in response to the primary magnetic field,
wherein the voltage response occurs at a primary frequency of the primary magnetic field.

6. The susceptometer of claim 1, further comprising a chamber in which the substrate, the electrodes, and the solenoid are disposed.

7. The susceptometer of claim 1, wherein the electrodes are moveably depressable such that the electrodes retract and remain in electrical contact with the sample.

8. The susceptometer of claim 1, wherein the electrodes are statically arranged in the substrate to be adepressable by the sample and provide electrical contact with the sample.

9. The susceptometer of claim 1, wherein the third pair of electrodes are arranged parallel to the set of aligned electrodes, and
the first pair of electrodes and the third pair of electrodes are arranged to obtain a Hall voltage of the sample.

10. The susceptometer of claim 1, wherein the plurality of electrodes further comprises a fourth pair of electrodes disposed on the substrate and being electrically conductive to engage and be in electrical contact with the sample,
wherein the third pair of electrodes and the fourth pair of electrodes are arranged to obtain a Hall voltage from the sample.

11. The susceptometer of claim 10, wherein half of the electrodes are current lines, and
half of the electrodes are voltage lines.

12. The susceptometer of claim 1, wherein the electrodes are electrically reconfigurable in-situ and in contact with the sample to obtain reconfigurably the Hall voltage of the sample and the current-in-plane resistance of the sample.

13. The susceptometer of claim 1, wherein the substrate electrically isolates the plurality of electrodes from each other.

14. The susceptometer of claim 1, further comprising the sample,
wherein the sample comprises a thin film.

15. The susceptometer of claim 1, further comprising the sample,
wherein the sample comprises a semiconductor thin film, a ferromagnetic thin film, or a combination comprising at least one of the foregoing.

16. The susceptometer of claim 1, wherein the primary magnetic field comprises a magnetic field direction that varies in response to the alternating current and is perpendicular to a surface of the sample that is in contact with the electrodes.

17. A susceptometer to perform magnetic susceptometry on a sample, the susceptometer comprising:
a chamber;
a substrate disposed in the chamber;
a plurality of electrodes disposed in the chamber and being electrically reconfigurable in-situ and in contact with the sample to obtain reconfigurably the Hall voltage of the sample and the current-in-plane resistance of the sample and to subject the sample to a direct current electrical current,
the plurality of electrodes comprising:
a first pair of electrodes disposed on the substrate and being electrically conductive to engage and be in electrical contact with the sample;
a second pair of electrodes disposed on the substrate and being electrically conductive to engage and be in electrical contact with the sample, the second pair of electrodes arranged collinear with the first pair of electrodes to form a set of aligned electrodes; and
a third pair of electrodes disposed on the substrate and being electrically conductive to engage and be in electrical contact with the sample, the third pair of electrodes arranged noncollinearly with set of aligned electrodes; and
a fourth pair of electrodes disposed on the substrate and being electrically conductive to engage and be in electrical contact with the sample, the fourth pair of electrodes arranged noncollinearly with set of aligned electrodes and arranged in a square pattern with the third pair of electrodes; and
a solenoid disposed in the chamber and circumscribingly disposed around the electrodes to:
receive the sample such that the solenoid is circumscribingly disposed around the sample;
receive an alternating current and produce a primary magnetic field based on the alternating current; and
subject the sample to the primary magnetic field.

18. A process for performing magnetic susceptometry on a sample, the process comprising:
providing the sample to a susceptometer comprising:
a substrate;
a plurality of electrodes comprising:
a first pair of electrodes disposed on the substrate and being electrically conductive to engage and be in electrical contact with the sample;
a second pair of electrodes disposed on the substrate and being electrically conductive to engage and be in electrical contact with the sample, the second pair of electrodes arranged collinear with the first pair of electrodes to form a set of aligned electrodes; and
a third pair of electrodes disposed on the substrate and being electrically conductive to engage and be in electrical contact with the sample, the third pair of electrodes arranged noncollinearly with set of aligned electrodes; and
a solenoid circumscribingly disposed around the electrodes;
receiving the sample in the solenoid such that the solenoid is circumscribingly disposed around the sample;
providing the solenoid with an alternating current;

producing, by the solenoid, a primary magnetic field in response to receiving the alternating current;
subjecting the sample to the primary magnetic field; and
subjecting the sample to a direct current electrical current to perform magnetic susceptometry.

19. The process of claim 18, further comprising measuring a Hall voltage of the sample.

20. The process of claim 18, further comprising measuring a current-in-plane resistance of the sample.

* * * * *